US009987346B2

(12) United States Patent
Massari et al.

(10) Patent No.: US 9,987,346 B2
(45) Date of Patent: Jun. 5, 2018

(54) METHODS AND COMPOSITIONS FOR VACCINATING A SUBJECT FOR A SEXUALLY TRANSMITTED PATHOGEN

(71) Applicants: Tufts University, Boston, MA (US); Boston Medical Center Corporation, Boston, MA (US); The Regents of the University of California, Oakland, CA (US)

(72) Inventors: Paola Massari, Cambridge, MA (US); Guillermo Madico, Natick, MA (US); Luis de la Maza, Irvine, CA (US)

(73) Assignees: Trustees of Tufts College, Medford, MA (US); Boston Medical Center Corporation, Boston, MA (US); The Regents of the University of California, Oakland, CA (US)

( * ) Notice: Subject to any disclaimer, the term of this patent is extended or adjusted under 35 U.S.C. 154(b) by 0 days. days.

(21) Appl. No.: 15/448,767

(22) Filed: Mar. 3, 2017

(65) Prior Publication Data

US 2017/0252424 A1 Sep. 7, 2017

Related U.S. Application Data

(60) Provisional application No. 62/303,075, filed on Mar. 3, 2016.

(51) Int. Cl.

| | |
|---|---|
| ***A61K 39/00*** | (2006.01) |
| ***A61K 39/02*** | (2006.01) |
| ***A61K 39/118*** | (2006.01) |
| ***C07K 14/22*** | (2006.01) |
| ***C07K 14/295*** | (2006.01) |

(52) U.S. Cl.
CPC ............ *A61K 39/118* (2013.01); *C07K 14/22* (2013.01); *C07K 14/295* (2013.01); *A61K 2039/55561* (2013.01); *A61K 2039/55566* (2013.01); *A61K 2039/575* (2013.01); *A61K 2039/6068* (2013.01)

(58) Field of Classification Search
CPC .................................................. A61K 39/118
See application file for complete search history.

(56) References Cited

PUBLICATIONS

Ahmed, K. et al., "Chlamydia Screening Among Sexually Active Young Female Enrollees of Health Plans—United States, 2000-2007," Morb. Mortal. Wkly. Rep., 58(14):362-5 (Apr. 17, 2009).
Andres, D. et al., "Partial protection against chlamydial reproductive tract infection by a recombinant major outer membrane protein/CpG/cholera toxin intranasal vaccine in the guinea pig Chlamydia caviae model," Journal of Reproductive Immunology, 91: 9-16 (2011).
Arnold, K. et al., "The Swiss-Model workspace: a web-based environment for protein structure homology modelling," Bioinformatics, 22(2):195-201 (Jan. 15, 2006).
Baher, W. et al., "Mapping antigenic domains expressed by Chlamydia trachomatis major outer membrane protein genes," Proc. Natl. Acad. Sci. U.S.A., 85(11):4000-4, PMCID:PMC280348 (Jun. 1988).
Bhasin, N. et al., "Neisseria meningitidis Lipopolysaccharide Modulates the Specific Humoral Immune Response to Neisserial Porins but Has No Effect on Porin-Induced Upregulation of Costimulatory Ligand B7-2," Infect.Immun. 69(8):5031-6 (Aug. 2001).
Biasini, M. et al., "Swiss-Model: modelling protein tertiary and quaternary structure using evolutionary information," Nucleic Acids Res. 42(Web Server issue):W252-W258. PMCID:PMC4086089 (Jul. 2014).
Boje, S. et al., "A multi-subunit Chlamydia vaccine inducing neutralizing antibodies and strong IFN-γ+CMI responses protects against a genital infection in minipigs," Immunology and Cell Biology, 94: 185-195 (2016).
Brunham, R. et al, "Immunology of Chlamydia Infection: Implications for a Chlamydia Trachomatis Vaccine," Nat. Rev. Immunol., 5(2):149-61 (Feb. 2005).
Brunham, R. et al., "The Unexpected Impact of a Chlamydia trachomatis Infection Control Program on Susceptibility to Reinfection," J. Infect. Dis., 192(10):1836-44 (Nov. 15, 2005).
Caldwell, H., et al., "Purification and Partial Characterization of the Major Outer Membrane Protein of Chlamydia trachomatis," Infect. Immun. Mar. 1981;31(3):1161-76.
Cambridge, C. et al., "Formulation, characterization, and expression of a recombinant MOMP Chlamydia trachomatis DNAvaccine encapsulated in chitosan nanoparticles," Int. J. Nanomedicine, 8:1759-71, PMCID: PMC3656902 (2013).
Carmichael, J. et al., "Induction of protection against vaginal shedding and infertility by a recombinant Chlamydia vaccine," Vaccine, 29(32):5276-83, PMCID:PMC3139009 (Jul. 18, 2011).
Cartwright, E. et al., "The Stonehouse survey: nasopharyngeal carnage of meningococci and Neisseria lactamica," Epidemiol. Infect. 99(3):591-601 (Dec. 1987).
Cheng, C. et al., "A vaccine formulated with a combination of TLR-2 and TLR-9 adjuvants and the recombinant major outer membrane protein elicits a robust immune response and significant protection against a C. muridarum challenge," Microbes. Infect., 16(3):244-52, PMCID:PMC3965591 (Mar. 2014).

(Continued)

*Primary Examiner* — Albert M Navarro
(74) *Attorney, Agent, or Firm* — Lawson & Weitzen, LLP; Sonia K. Guterman

(57) ABSTRACT

Purified *Chlamydia* major outer membrane protein (MOMP) has been observed to induce protection against genital and respiratory challenge in mice. MOMP contains variable domains that are highly immunogenic and elicit cross-serovar neutralizing monoclonal and polyclonal antibodies and T cell responses in animal and human models. Examples herein provide a method for vaccinating a subject against *Chlamydia* using a composition that is a recombinant *Neisseria* porin that contains at least one antigenic variable domain of *Chlamydia*. The variable domains are inserted into the amino acid sequence of the *Neisseria* porin at a position encoding a surface-exposed loop of the *Neisseria* porin. The vaccine further contains an adjuvant that induces a Th1 response greater than a Th2 response.

21 Claims, 17 Drawing Sheets

(56) References Cited

PUBLICATIONS

Childs, T. et al., "In vitro assessment of halobacterial gas vesicles as a Chlamydia vaccine display and delivery system," Vaccine, 30(41):5942-8 (Sep. 7, 2012).
Deasy, A. et al., "Nasal Inoculation of the Commensal Neisseria lactamica Inhibits Carriage of Neisseria meningitidis by Young Adults: A Controlled Human Infection Study," Clin.Infect.Dis. 60(10):1512-20 (May 15, 2015).
Dixit, S. et al., "Poly (lactic acid)-poly (ethylene glycol) nanoparticles provide sustained delivery of a Chlamydia trachomatis recombinant MOMP peptide and potentiate systemic adaptive immune responses in mice." Nanomedicine (Mar. 4, 2014).
Dunne, D. et al., "What About Men?" Sex. Transm. Dis., 35(11 Suppl):S1-S2 (Nov. 2008).
Dong-Ji, Z. et al., "Priming with Chlamydia trachomatis Major Outer Membrane Protein (MOMP) DNA followed by MOMP ISCOM Boosting Enhances Protection and is Associated with Increased Immunoglobulin A and Th1 Cellular Immune Responses," Infect. Immun., 8(6):3074-8, PMCID:PMC97534 (Jun. 2000).
Fairley, S., et al., "Chlamydia trachomatis recombinant MOMP encapsulated in PLGA nanoparticles triggers primarily T helper 1 cellular and antibody immune responses in mice: a desirable candidate nanovaccine," Int. J. Nanomedicine, 8:2085-99, PMCID:PMC3682632 (2013).
Farris, C. et al., "CD4_T Cells and Antibody Are Required for Optimal Major Outer Membrane Protein Vaccine-Induced Immunity to Chlamydia muridarum Genital Infection," Infect. Immun., 78(10):4374-83, PMCID:PMC2950360 (Oct. 2010).
Farris, C. et al., "Vaccination against Chlamydia Genital Infection Utilizing the Murine C. muridarum Model," Infect. Immun., 79(3):986-96, PMCID:PMC3067520 (Mar. 2011).
Feher, V. et al., "A 3-Dimensional Trimeric Beta-Barrel Model for Chlamydia MOMP Contains Conserved and Novel Elements of Gram-Negative Bacterial Porins," PLoS ONE, 8(7): e68934, PMCID:PMC3723809 (2013).
Gold, R. et al., "Carriage of Neisseria meningitidis and Neisseria lactamica in Infants and Children," J.Infect.Dis. 137(2):112-21 (Feb. 1978).
Gotz, H. et al., "Is the Increase in Notifications of Chlamydia trachomatis Infections in Sweden the Result of Changes in Prevalence, Sampling Frequency or Diagnostic Methods?" Scand. J. Infect. Dis., 34(1):28-34 (2002).
Grayston, J. et al., "The Potential for Vaccine against Infection of the Genital Tract with Chlamydia trachomatis," Sex. Transm. Dis., 5(2):73-7 (Apr. 1978).
Greenwood, F. et al., "The Preparation of 131I-Labelled Human Growth Hormone of High Specific Radioactivity," Biochem. J., 89:114-22 (1963).
Igietseme, J. et al., "Induction of Protective Immunity against Chlamydia trachomatis Genital Infection by a Vaccine Based on Major Outer Membrane Protein—Lipophilic Immune Response-Stimulating Complexes," Infect. Immun., 68(12):6798-806, PMCID:PMC97783 (Dec. 2000).
Jiang, P. et al., "Hepatitis B virus core antigen as a carrier for Chlamydia trachomatis MOMP multi-epitope peptide enhances protection against genital chlamydial infection," Oncotarget, 6(41): 43281-92 (2013).
Kalbina, I. et al., "A novel chimeric MOMP antigen expressed in *Escherichia coli*, *Arabidopsis thaliana*, and Daucus carota as a potential Chlamydia trachomatis vaccine candidate," Protein Expr. Purif, 80(2):194-202 (Dec. 2011).
Kari, L. et al., "Chlamydia trachomatis Native Major Outer Membrane Protein Induces Partial Protection in Nonhuman Primates: Implication for a Trachoma Transmission-Blocking Vaccine," J. Immunol., 182(12):8063-70, PMCID:PMC2692073 (Jun. 15, 2009).
Kattner, C. et al. "Crystallographic analysis of Neisseria meningitidis PorB extracellular loops potentially implicated in TLR2 recognition," J. Struct Biol., 185(3):440-447 (2014).
Kattner, C. et al., "One-Step Purification and Porin Transport Activity of the Major Outer Membrane Proteins P2 from Haemophilus influenzae, FomA from Fusobacterium nucleatum and PorB from Neisseria meningitides," Appl. Biochem.Biotechnol. 175(6): 2907-15 (Mar. 2015).
Kim, S. et al., "Epitope clusters in the major outer membrane protein of Chlamydia trachomatis," Curr.Opin.Immunol. 13(4):429-36 (Aug. 2001).
Klinman, D. et al., Int. Rev. Immunol., "Adjuvant Activity of CpG Oligodeoxynucleotides," 25(3-4):135-54 (May 2006).
Li, W. et al., "Induction of Cross-Serovar Protection against Genital Chlamydial Infection by a Targeted Multisubunit Vaccination Approach," Clin. Vaccine Immunol., 14(12):1537-44, PMCID:PMC2168373 (Dec. 2007).
Li, Y. et al., "Immunization with Live Neisseria lactamica Protects Mice against Meningococcal Challenge and Can Elicit Serum Bactericidal Antibodies," Infect.Immun. 74(11):6348-55 (Nov. 2006).
Liu, X. et al., "The PorB porin from commensal Neisseria lactamica induces Th1 and Th2 immune responses to ovalbumin in mice and is a potential immune adjuvant," Vaccine 26(6):786-96 (Feb. 6, 2008).
Liu, X. et al., "Human Airway Epithelial Cell Responses to Neisseria lactamica and Purified Porin via Toll-Like Receptor 2-Dependent Signaling," Infect. Immun. 78(12):5314-23. PMCID:PMC2982390 (Dec. 2010).
Longbottom, D. et al., "Vaccination against chlamydial infections of man and animals," Vet. J., 171(2):263-75 (Mar. 2006).
MacDonald, B. et al., "Immune Response of Owl Monkeys to Topical Vaccination with Irradiated Chlamydia trachomatis," J. Infect. Dis., 149(3):439-42 (Mar. 1984).
Madico, G. et al., "Factor H Binding and Function in Sialylated Pathogenic Neisseriae is Influenced by Gonococcal, out Not Meningococcal, Porin," J.Immunol. 178(7):4489-97 (Apr. 1, 2007).
Massari, P. et al., "Cutting Edge: Immune Stimulation by Neisserial Porins is Toll-Like Receptor 2 and MyD88 Dependent," J. Immunol 168(4): 1533-7 (Feb. 2002).
Massari, P. et al., "Improved purification of native meningococcal porin PorB and studies on its structure/function," Protein Expr. Purif. 44(2): 136-46 (Dec. 2005).
Massari, P. et al., "Toll-Like Receptor 2-Dependent Activity of Native Major Outer Membrane Protein Proteosomes of Chlamydia trachomatis," Infect. Immun., 81(1):303-10, PMCID:PMC3536141 (Jan. 2013).
Miles, A. et al., "Montanide® ISA 720 vaccines: quality control of emulsions, stability of formulated antigens, and comparative immunogenicity of vaccine formulations," Vaccine, 23(19):2530-39 (Mar. 31, 2005).
Miller, W. et al., "Prevalence of Chlamydial and Gonococcal Infections Among Young Adults in the United States," JAMA, 291(18):2229-36 (May 12, 2004).
Motin, V. et al., "Immunization with a Peptide Corresponding to Chlamydial Heat Shock Protein 60 Increases the Humoral Immune Response in C3H Mice to a Peptide Representing Variable Domain 4 of the Major Outer Membrane Protein of Chlamydia trachomatis," Clinical and Diagnostic Laboratory Immunology, 6(3): 356-63 (1999).
Murdin, A. et al., "A Poliovirus Hybrid Expressing a Neutralization Epitope from the Major Outer Membrane Protein of Chlamydia trachomatis is Highly Immunogenic," Infection and Immunity, 61(10): 4406-14 (1993).
Nunes, A. et al., "Adaptive Evolution of the Chlamydia trachomatis Dominant Antigen Reveals Distinct Evolutionary Scenarios for B- and T-cell Epitopes: Worldwide Survey," PLoS ONE, 5(10), PMCID:PMC2950151 (2010).
Oliver, K. et al., "Neisseria lactamica Protects against Experimental Meningococcal Infection," Infect.Immun. 70 (7):3621-6 (Jul. 2002).

(56) References Cited

OTHER PUBLICATIONS

Olsen, A. et al., "Protection Against Chlamydia trachomatis Infection and Upper Genital Tract Pathological Changes by Vaccine-Promoted Neutralizing Antibodies Directed to the VD4 of the Major Outer Membrane Protein," J. Infect. Dis., 212(6): 978-989, (Mar. 6, 2015).
O'Meara, C. et al., "Immunization with a MOMP-Based Vaccine Protects Mice against a Pulmonary Chlamydia challenge and Identifies a Disconnection between Infection and Pathology," PLoS One, 8(4): e61962 (2013).
Ortiz, L. et al., "T-Cell Epitopes in Variable Segments of Chlamydia trachomatis Major Outer Membrane Protein Elicit Serovar-Specific Immune Responses in Infected Humans," Infect. Immun., 68(3):1719-23, PMCID:PMC97337 (Mar. 2000).
Ou, C. et al., "The imbalance of Th17/Treg in Chinese children with Henoch-Schonlein purpura," International Immunopharmacology, 16: 505-513 (2013).
Pal, S. et al., "Protection against Infertility in a BALB/c Mouse Salpingitis Model by Intranasal Immunization with the Mouse Pneumonitis Biovar of Chlamydia trachomatis," Infect. Immun., 62(8):3354-62, PMCID:PMC302966 (Aug. 1994).
Pal, S. et al., "Immunization with an Acellular Vaccine Consisting of the Outer Membrane Complex of Chlamydia trachomatis Induces Protection against a Genital Challenge," Infection and Immunity, 65(8): 3361-69 (1997).
Pal, S. et al., "Monoclonal immunoglobulin A antibody to the major outer membrane protein of the Chlamydia trachomatis mouse pneumonitis biovar protects mice against a chlamydial genital challenge," Vaccine, 15(5):575-82 (Apr. 1997).
Pal, S. et al., "Vaccination of mice with DNA plasmids coding for the Chlamydia trachomatis major outer membrane protein elicits an immune response but fails to protect against a genital challenge," Vaccine, 17(5):459-65 (Feb. 5, 1999).
Pal, S. et al., "Immunization with the Chlamydia trachomatis Mouse Pneumonitis Major Outer Membrane Protein Can Elicit a Protective Immune Response against a Genital Challenge," Infect Immun., 69(10):6240-7. PMCID:PMC98757 (Oct. 2001).
Pal, S. et al., "Immunization with the Chlamydia trachomatis Mouse Pneumonitis Major Outer Membrane Protein by Use of CpG Oligodeoxynucleotides as an Adjuvant Induces a Protective Immune Response against an Intranasal Chlamydial Challenge," Infect. Immun., 70(9):4812-7, PMCID:PMC128273 (Sep. 2002).
Pal, S. et al., "New Murine Model for the Study of Chlamydia trachomatis Genitourinary Tract Infections in Males," Infect. Immun., 72(7):4210-6, PMCID:PMC427456 (Jul. 2004).
Pal, S. et al., "Vaccination with the Chlamydia trachomatis Major Outer Membrane Protein Can Elicit an Immune Response as Protective as That Resulting from Inoculation with Live Bacteria," Infect. Immun., 73(12):8153-60, PMCID: PMC1307068 (Dec. 2005).
Pal, R. et al., "Definitive toxicology and biodistribution study of a polyvalent DNA prime/protein boost human Immunodeficiency virus type 1 (HIV-1) vaccine in rabbits," Vaccine, 24(6):766-75 (Feb. 6, 2006).
Peterson, E. et al., "Functional and Structural Mapping of Chlamydia trachomatis Species-Specific Major Outer Membrane Protein Epitopes by Use of Neutralizing Monoclonal Antibodies," Infect. Immun., 59(11):4147-53, PMCID: PMC259009 (Nov. 1991).
Plummer, F. et al., "Cofactors in Male-Female Sexual Transmission of Human Immunodeficiency Virus Type 1," J. Infect. Dis., 163(2):233-9 (Feb. 1991).
Ralli-Jain, P. et al., "Enhancement of the protective efficacy of a Chlamydia trachomatis recombinant vaccine by combining systemic and mucosal routes for immunization," Vaccine, 28(48):7659-66, PMCID:PMC2981640 (Nov. 10, 2010).
Rodriguez-Maranon, M. et al., "Prediction of the membrane-spanning beta-strands of the major outer membrane protein of Chlamydia," Protein Sci., 11(7):1854-61. PMCID:PMC2373662 (Jul. 2002).
Schachter, J., "Chlamydial Infections," N. Engl. J. Med., 298(8):428-35 (Feb. 23, 1978).
Schacter, J. et al., "Elimination of blinding trachoma," Curr. Opin. Infect. Dis.; 15(5):491-5 (Oct. 2002).
Schautteet, K. et al., "Protection of pigs against Chlamydia trachomatis challenge by administration of a MOMP-based DNA vaccine in the vaginal mucosa," Vaccine, 29: 1399-1407 (2011).
Shaw, J. et al., "Dendritic Cells Pulsed with a Recombinant Chlamydial Major Outer Membrane Protein Antigen Elicit a CD4 Type 2 Rather than Type 1 Immune Response That is Not Protective," Infect. Immun., 70(3):1097-105, PMCID: PMC127771 (Mar. 2002).
Singh, S. et al., "Mucosal immunization with recombinant MOMP genetically linked with modified cholera toxin confers protection against Chlamydia trachomatis infection," Vaccine, 24(8):1213-24 (Feb. 20, 2006).
Stephens, R. et al., "Diversity of Chlamydia trachomatis Major Outer Membrane Protein Genes," J.Bacteriol., 169:3879-85 (1987).
Su, H. et al., "Identification and Characterization of T Helper Cell Epitopes of the Major Outer Membrane Protein of Chlamydia trachomatis," J. Exp. Med., 172:203-12 (1990).
Su, H. et al., "Immunogenicity of a synthetic oligopeptide corresponding to antigenically common T-helper and B-cell neutralizing epitopes of the major outer membrane protein of Chlamydia trachomatis," Vaccine, 11(11):1159-66 (1993).
Su, H. et al., "Immunogenicity of a Chimeric Peptide Corresponding to T Helper and B Cell Epitopes of the Chlamych'a trachomatis Major Outer Membrane Protein," J. Exp. Med.,;175(1):227-35, PMCID:PMC2119084 (Jan. 1, 1992).
Su, H. et al., "Protective efficacy of a parenterally administered MOMP-derived synthetic oligopeptide vaccine in a murine model of Chlamydia trachomatis genital tract infection: serum neutralizing IgG antibodies do not protect against chlamydial genital tract infection," Vaccine, 13(11):1023-32 (Aug. 1995).
Sun, G. et al., "Structural and Functional Analyses of the Major Outer Membrane Protein of Chlamydia trachomatis," J. Bacteriol., 189(17):6222-35, PMCID:PMC1951919 (Sep. 2007).
Taylor, H. et al., "Oral Immunization With Chlamydial Major Outer Membrane Protein (MOMP)," Investigative Ophthalmology & Visual Science, 29(12): 1847-1853 (1988).
Tifrea, D. et al., "Amphipols stabilize the Chlamydia major outer membrane protein and enhance its protective ability as a vaccine," Vaccine, 29(28):4623-31, PMCID:PMC3114171 (Jun. 20, 2011).
Tifrea, D. et al., "Vaccination with the Recombinant Major Outer Membrane Protein Elicits Antibodies to the Constant Domains and Induces Cross-Serovar Protection against Intranasal Challenge with Chlamydia Trachomatis," Infect. Immun., 81(5):1741-50, PMCID:PMC3648024 (May 2013).
Tifrea, D. et al., "Vaccination with major outer membrane protein proteosomes elicits protection in mice against a Chlamydia respiratory challenge," Microbes. Infect., 15(13):920-7, PMCID:PMC3842390 (Nov. 2013).
Torrone, E. et al., "Prevalence of Chlamydia trachomatis Genital Infection Among Persons Aged 14-39 Years—United States, 2007-2012," Morb. Mortal. Wkly. Rep., 63(38):834-38 (Sep. 26, 2014).
Toussi, D. et al., "The Amino Acid Sequence of Neisseria lactamica PorB SurfaceExposed Loops Influences Toll-Like Receptor 2-Dependent Cell Activation," Infect. Immun. 80(10):341728. PMCID:PMC3457564 (Oct. 2012).
Toussi, D. et al., "Immune Adjuvant Effect of Molecularly-defined Toll-Like Receptor Ligands," Vaccines, 2(2):323-53 (2014).
Troncosco, G. et al., "Analysis of Neisseria lactamica antigens putatively implicated in acquisition of natural immunity to Neisseria meningitides," FEMS Immunol.Med.Microbiol. 34(1):9-15 (Sep. 6, 2002).
Tu, J. et al., "A multi-epitope vaccine based on Chlamydia trachomatis major outer membrane protein induces specific immunityin mice," Acta Biochim. Biophys. Sin. (Shanghai) 46(5): 401-408 (Mar. 28, 2014).
Vaughan, A. et al., "Neisseria lactamica Selectively Induces Mitogenic Proliferation of the Naive B Cell Pool via Cell Surface Ig," J.Immunol. 185(6):3652-60 (Sep. 15, 2010).

(56) References Cited

OTHER PUBLICATIONS

Wang, S. et al., "Immunotyping of Chlamydia trachomatis with Monoclonal Antibodies," J.Infect.Dis. 152(4):791-800 (Oct. 1985).
Wang, S. et al., "Pannus with experimental trachoma and inclusion conjunctivitis agent infection of Taiwan monkeys," Am. J. Ophthalmol., 63(5): Suppl-45, 1133-45 (May 1967).
Westrom, L. et al., "Chlamydia and its effect on reproduction," J. Br. Fer. Soc.; 1(1):23-30 (1996). Abstract only available.
Xu, W. et al., "Protective immunity against Chlamydia trachomatis genital infection induced by a vaccine based on the major outer membrane multi-epitope human papillomavirus major capsid protein L1," Vaccine, 29(15): 2672-78 (2011).
Yu, H. et al., "Evaluation of a multisubunit recombinant polymorphic membrane protein and major outer membrane protein T cell vaccine against Chlamydia muridarum genital infection in three strains of mice," Vaccine, 32(36): 4672-80 (Aug. 6, 2014).
Zhang, Y., et al., "Protective monoclonal antibodies recognize epitopes located on the major outer membrane protein of Chlamydia trachomatis," J.Immunol. 138(2):575-81 (Jan. 15, 1987).
Zhang, D. et al., "DNA Vaccination with the Major Outer-Membrane Protein Gene Induces Acquired Immunity to chlamydia trachomatis (Mouse Pneumonitis) Infection," Journal of Infectious Diseases, 176: 1035-40 (Oct. 1997).
Zhang X. et al., "Protective efficacy against Chlamydophila psittaci by oral immunization based on transgenic rice expressing MOMP in mice," Vaccine, 31(4):698-703 (Jan. 11, 2013).
Zhong, g. et al., "Immunoaccessible Peptide Sequences of the Major Outer Membrane Protein from Chlamydia trachomatis Serovar C ," Infect. Immun., 58(5):1450, PMCID:PMC258646 (May 1990).
Zhu, et al., "Hepatitis B virus surface antigen as delivery vector can enhance Chlamydia trachomatis MOMP multi-epitope immune response in mice," Appl. Microbial. Biotechnol., 98(9):4107-17 (May 2014).

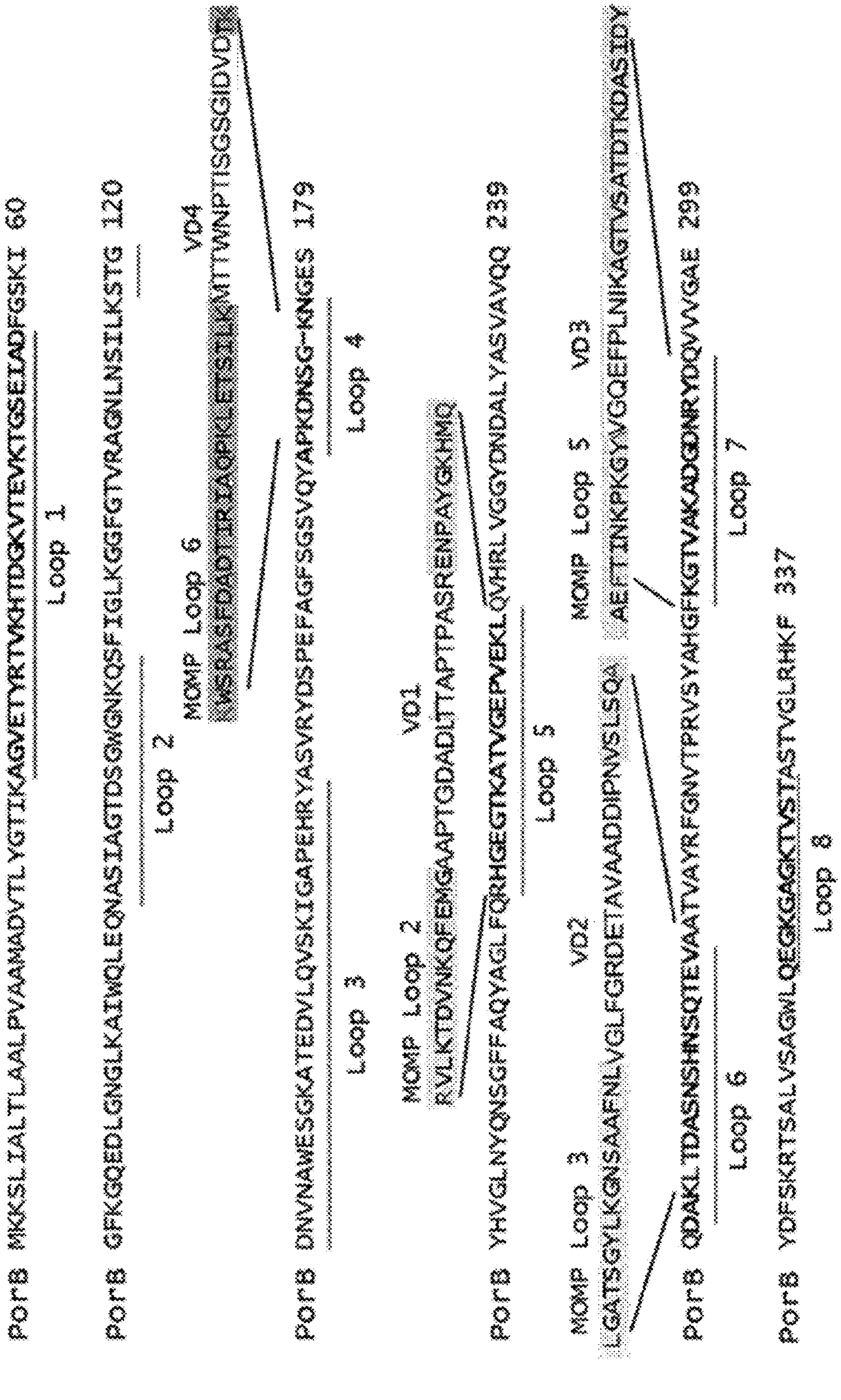

Figure 1A

```
PorB   MKKSLIALTLAALPVAAMADVTLYGTIKAGVETYRTVKHTDGKVTEVKTGSEIADFGSKI  60
                              Loop 1

PorB   GFKGQEDLGNGLKAIWQLEQNASIAGTDSGWGNKQSFIGLKGGFGTVRAGNLNSILKSTG  120
                      Loop 2                                  VD4
                                                      MOMP Loop 6
PorB   DNVNAWESGKATEDVLQVSKIGAPEHRYASVRYDSPEFAGFSGSVQYAPKDNSG-KNGES  179
                Loop 3                                           Loop 4
       MOMP Loop 2        VD1
PorB   RVLKTDVNKQEMGAAPTGDADITAPTPASRENPAYGKHMQVHRLVGGYDNDALYASVAVQQ  239
                           Loop 5
                                              MOMP Loop 5    VD3
PorB   AEFTTNKPKGYVGQEFPLNIKAGTVAKADGDNRYDQVVVGAE  299
                                              Loop 7
       MOMP Loop 3         VD2
PorB   QDAKLTDASNSHNSQTEVAATVAYRFGNVTPRVSYAHGFKGTVSTASTVGLRHKF  337
                Loop 6                          Loop 8

PorB   YDFSKRTSALVSAGWLQEGKGAGKTVSTASTVGLRHKF  337
```

WSRASFDADTIP TAQFKLETSTLKMTTWNPTISGSGIDVDT (VD4 highlighted)

AEFTTNKPKGYVGQEFPLNIKAGTVSATDTKDASIDY (VD3 highlighted)

(cont.)

PorB/VD1

MOMP VD1 in PorB L5

PorB/VD2

MOMP VD2 in PorB L6

PorB/VD3

MOMP VD3 in PorB L7

Figure 13A
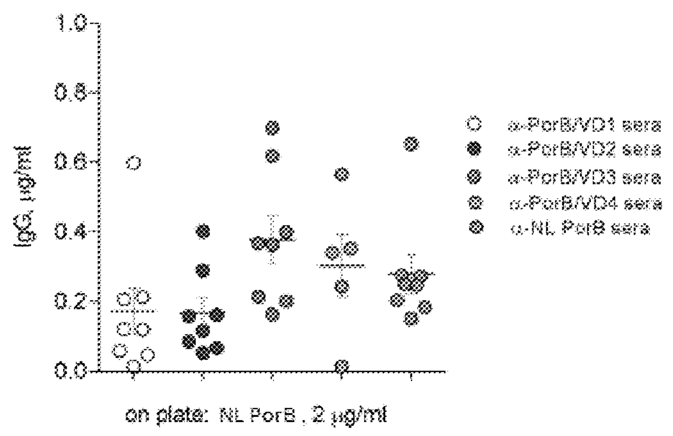
Figure 13B
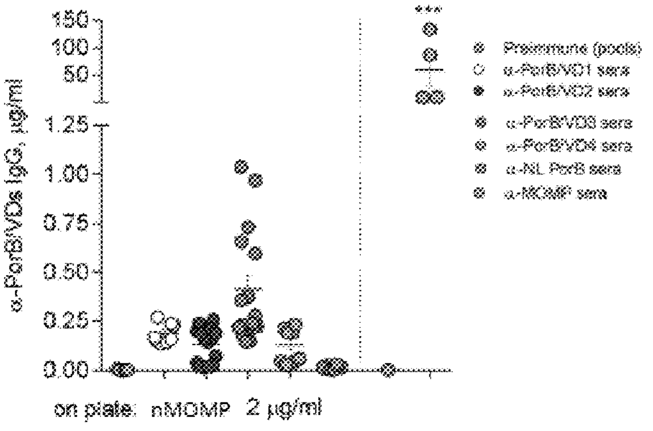
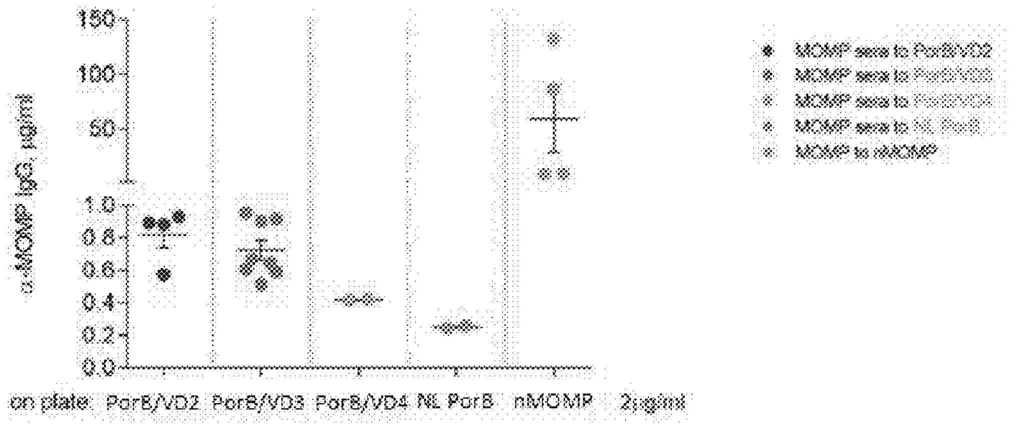
Figure 13C

SEQUENCE LISTING

```
<160> NUMBER OF SEQ ID NOS: 14

<210> SEQ ID NO 1
<211> LENGTH: 337
<212> TYPE: PRT
<213> ORGANISM: Artificial Sequence
<220> FEATURE:
<223> OTHER INFORMATION: The amino acid sequence was designed and
      synthesized

<400> SEQUENCE: 1

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Tyr Arg Thr Val Lys His Thr Asp Gly Lys Val Thr Glu Val Lys
        35                  40                  45

Thr Gly Ser Glu Ile Ala Asp Phe Gly Ser Lys Ile Gly Phe Lys Gly
    50                  55                  60
```

-continued

```
Gln Glu Asp Leu Gly Asn Gly Leu Lys Ala Ile Trp Gln Leu Glu Gln
65                  70                  75                  80

Asn Ala Ser Ile Ala Gly Thr Asp Ser Gly Trp Gly Asn Lys Gln Ser
                85                  90                  95

Phe Ile Gly Leu Lys Gly Gly Phe Gly Thr Val Arg Ala Gly Asn Leu
            100                 105                 110

Asn Ser Ile Leu Lys Ser Thr Gly Asp Asn Val Asn Ala Trp Glu Ser
        115                 120                 125

Gly Lys Ala Thr Glu Asp Val Leu Gln Val Ser Lys Ile Gly Ala Pro
    130                 135                 140

Glu His Arg Tyr Ala Ser Val Arg Tyr Asp Ser Pro Glu Phe Ala Gly
145                 150                 155                 160

Phe Ser Gly Ser Val Gln Tyr Ala Pro Lys Asp Asn Ser Gly Lys Asn
                165                 170                 175

Gly Glu Ser Tyr His Val Gly Leu Asn Tyr Gln Asn Ser Gly Phe Phe
            180                 185                 190

Ala Gln Tyr Ala Gly Leu Phe Gln Arg His Gly Glu Gly Thr Lys Ala
        195                 200                 205

Thr Val Gly Glu Pro Val Glu Lys Leu Gln Val His Arg Leu Val Gly
    210                 215                 220

Gly Tyr Asp Asn Asp Ala Leu Tyr Ala Ser Val Ala Val Gln Gln Gln
225                 230                 235                 240

Asp Ala Lys Leu Thr Asp Ala Ser Asn Ser His Asn Ser Gln Thr Glu
                245                 250                 255

Val Ala Ala Thr Val Ala Tyr Arg Phe Gly Asn Val Thr Pro Arg Val
            260                 265                 270

Ser Tyr Ala His Gly Phe Lys Gly Thr Val Ala Lys Ala Asp Gly Asp
        275                 280                 285

Asn Thr Tyr Asp Gln Val Val Val Gly Ala Glu Tyr Asp Phe Ser Lys
    290                 295                 300

Arg Thr Ser Ala Leu Val Ser Ala Gly Trp Leu Gln Glu Gly Lys Gly
305                 310                 315                 320

Ala Gly Lys Thr Val Ser Thr Ala Ser Thr Val Gly Leu Arg His Lys
                325                 330                 335

Phe


<210> SEQ ID NO 2
<211> LENGTH: 437
<212> TYPE: PRT
<213> ORGANISM: Artificial Sequence
<220> FEATURE:
<223> OTHER INFORMATION: The amino acid sequence was designed and
      synthesized

<400> SEQUENCE: 2

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Tyr Arg Thr Val Lys His Thr Asp Gly Lys Val Thr Glu Val Lys
        35                  40                  45

Thr Gly Ser Glu Ile Ala Asp Phe Gly Ser Lys Ile Gly Phe Lys Gly
    50                  55                  60

Gln Glu Asp Leu Gly Asn Gly Leu Lys Ala Ile Trp Gln Leu Glu Gln
65                  70                  75                  80
```

-continued

```
Asn Ala Ser Ile Ala Gly Thr Asp Ser Gly Trp Gly Asn Lys Gln Ser
                85                  90                  95

Phe Ile Gly Leu Lys Gly Gly Phe Gly Thr Val Arg Ala Gly Asn Leu
            100                 105                 110

Asn Ser Ile Leu Lys Ser Thr Gly Asp Asn Val Asn Ala Trp Glu Ser
        115                 120                 125

Gly Lys Ala Thr Glu Asp Val Leu Gln Val Ser Lys Ile Gly Ala Pro
    130                 135                 140

Glu His Arg Tyr Ala Ser Val Arg Tyr Asp Ser Pro Glu Phe Ala Gly
145                 150                 155                 160

Phe Ser Gly Ser Val Gln Tyr Lys Trp Ser Arg Ala Ser Phe Asp Ala
                165                 170                 175

Asp Thr Ile Arg Ile Ala Gln Pro Lys Leu Glu Thr Ser Ile Leu Lys
            180                 185                 190

Met Thr Thr Trp Asn Pro Thr Ile Ser Gly Ser Gly Ile Asp Val Asp
        195                 200                 205

Thr Lys Tyr His Val Gly Leu Asn Tyr Gln Asn Ser Gly Phe Phe Ala
    210                 215                 220

Gln Tyr Ala Gly Leu Phe Gln Arg Val Leu Lys Thr Asp Val Asn Lys
225                 230                 235                 240

Gln Phe Glu Met Gly Ala Ala Pro Thr Gly Asp Ala Asp Leu Thr Thr
                245                 250                 255

Ala Pro Thr Pro Ala Ser Arg Glu Asn Pro Ala Tyr Gly Lys His Met
            260                 265                 270

Gln Val His Arg Leu Val Gly Gly Tyr Asp Asn Asp Ala Leu Tyr Ala
        275                 280                 285

Ser Val Ala Val Gln Gln Gln Leu Gly Ala Thr Ser Gly Tyr Leu Lys
    290                 295                 300

Gly Asn Ser Ala Ala Phe Asn Leu Val Gly Leu Phe Gly Arg Asp Glu
305                 310                 315                 320

Thr Ala Val Ala Ala Asp Asp Ile Pro Asn Val Ser Leu Ser Gln Ala
                325                 330                 335

Ala Thr Val Ala Tyr Arg Phe Gly Asn Val Thr Pro Arg Val Ser Tyr
            340                 345                 350

Ala His Gly Ala Glu Phe Thr Ile Asn Lys Pro Lys Gly Tyr Val Gly
        355                 360                 365

Gln Glu Phe Pro Leu Asn Ile Lys Ala Gly Thr Val Ser Ala Thr Asp
    370                 375                 380

Thr Lys Asp Ala Ser Ile Asp Tyr Gln Val Val Val Gly Ala Glu Tyr
385                 390                 395                 400

Asp Phe Ser Lys Arg Thr Ser Ala Leu Val Ser Ala Gly Trp Leu Gln
                405                 410                 415

Glu Gly Lys Gly Ala Gly Lys Thr Val Ser Thr Ala Ser Thr Val Gly
            420                 425                 430

Leu Arg His Lys Phe
        435
```

<210> SEQ ID NO 3
<211> LENGTH: 28
<212> TYPE: PRT
<213> ORGANISM: Artificial Sequence
<220> FEATURE:
<223> OTHER INFORMATION: The amino acid sequence was designed and synthesized

<400> SEQUENCE: 3

```
Ala Gly Val Glu Thr Tyr Arg Thr Val Lys His Thr Asp Gly Lys Val
1               5                   10                  15

Thr Glu Val Lys Thr Gly Ser Glu Ile Ala Asp Phe
            20                  25
```

<210> SEQ ID NO 4
<211> LENGTH: 15
<212> TYPE: PRT
<213> ORGANISM: Artificial Sequence
<220> FEATURE:
<223> OTHER INFORMATION: The amino acid sequence was designed and synthesized

<400> SEQUENCE: 4

```
Asn Ala Ser Ile Ala Gly Thr Asp Ser Gly Trp Gly Asn Lys Gln
1               5                   10                  15
```

<210> SEQ ID NO 5
<211> LENGTH: 28
<212> TYPE: PRT
<213> ORGANISM: Artificial Sequence
<220> FEATURE:
<223> OTHER INFORMATION: The amino acid sequence was designed and synthesized

<400> SEQUENCE: 5

```
Asp Asn Val Asn Ala Trp Glu Ser Gly Lys Ala Thr Glu Asp Val Leu
1               5                   10                  15

Gln Val Ser Lys Ile Gly Ala Pro Glu His Arg Tyr
            20                  25
```

<210> SEQ ID NO 6
<211> LENGTH: 9
<212> TYPE: PRT
<213> ORGANISM: Artificial Sequence
<220> FEATURE:
<223> OTHER INFORMATION: The amino acid sequence was designed and synthesized

<400> SEQUENCE: 6

```
Ala Pro Lys Asp Asn Ser Gly Lys Asn
1               5
```

<210> SEQ ID NO 7
<211> LENGTH: 18
<212> TYPE: PRT
<213> ORGANISM: Artificial Sequence
<220> FEATURE:
<223> OTHER INFORMATION: The amino acid sequence was designed and synthesized

<400> SEQUENCE: 7

```
Arg His Gly Glu Gly Thr Lys Ala Thr Val Gly Glu Pro Val Glu Lys
1               5                   10                  15

Leu Gln
```

<210> SEQ ID NO 8
<211> LENGTH: 17
<212> TYPE: PRT
<213> ORGANISM: Artificial Sequence
<220> FEATURE:
<223> OTHER INFORMATION: The amino acid sequence was designed and synthesized

<400> SEQUENCE: 8

Asp Ala Lys Leu Thr Asp Ala Ser Asn Ser His Asn Ser Gln Thr Glu
1 5 10 15

Val

<210> SEQ ID NO 9
<211> LENGTH: 15
<212> TYPE: PRT
<213> ORGANISM: Artificial Sequence
<220> FEATURE:
<223> OTHER INFORMATION: The amino acid sequence was designed and synthesized

<400> SEQUENCE: 9

Phe Lys Gly Thr Val Ala Lys Ala Asp Gly Asp Asn Thr Tyr Asp
1 5 10 15

<210> SEQ ID NO 10
<211> LENGTH: 12
<212> TYPE: PRT
<213> ORGANISM: Artificial Sequence
<220> FEATURE:
<223> OTHER INFORMATION: The amino acid sequence was designed and synthesized

<400> SEQUENCE: 10

Gln Glu Gly Lys Gly Ala Gly Lys Thr Val Ser Thr
1 5 10

<210> SEQ ID NO 11
<211> LENGTH: 18
<212> TYPE: PRT
<213> ORGANISM: Artificial Sequence
<220> FEATURE:
<223> OTHER INFORMATION: The amino acid sequence was designed and synthesized

<400> SEQUENCE: 11

Ala Ala Pro Thr Gly Asp Ala Asp Leu Thr Thr Ala Pro Thr Pro Ala
1 5 10 15

Ser Arg

<210> SEQ ID NO 12
<211> LENGTH: 18
<212> TYPE: PRT
<213> ORGANISM: Artificial Sequence
<220> FEATURE:
<223> OTHER INFORMATION: The amino acid sequence was designed and synthesized

<400> SEQUENCE: 12

Val Gly Leu Phe Gly Arg Asp Glu Thr Ala Val Ala Ala Asp Asp Ile
1 5 10 15

Pro Asn

<210> SEQ ID NO 13
<211> LENGTH: 10
<212> TYPE: PRT
<213> ORGANISM: Artificial Sequence
<220> FEATURE:
<223> OTHER INFORMATION: The amino acid sequence was designed and synthesized -continued

```
<400> SEQUENCE: 13

Val Gly Gln Glu Phe Pro Leu Asn Ile Lys
1               5                   10


<210> SEQ ID NO 14
<211> LENGTH: 16
<212> TYPE: PRT
<213> ORGANISM: Artificial Sequence
<220> FEATURE:
<223> OTHER INFORMATION: The amino acid sequence was designed and
      synthesized

<400> SEQUENCE: 14

Met Thr Thr Trp Asn Pro Thr Ile Ser Gly Ser Gly Ile Asp Val Asp
1               5                   10                  15
```

METHODS AND COMPOSITIONS FOR VACCINATING A SUBJECT FOR A SEXUALLY TRANSMITTED PATHOGEN

RELATED APPLICATIONS

The present invention claims the benefit of provisional application No. 62/303,075 filed Mar. 3, 2016 "Methods and compositions for vaccinating a subject for a sexually transmitted pathogen" by inventors Paola Massari, Guillermo Madico, and Luis de la Maza which is hereby incorporated by reference herein in its entirety.

GOVERNMENT SUPPORT CLAUSE

This invention was made with government support under grant AI123885 awarded by the National Institutes of Health. The government has certain rights in the invention.

BACKGROUND

*Chlamydia trachomatis* is an obligate intracellular gram-negative organism that is the leading cause of bacterial sexually transmitted infections worldwide. In the United States, the Center for Disease Control reported over 1.4 million cases of *Chlamydia* in 2013. See, Miller et al., *JAMA,* 291(18):2229-36 (2004); Ahmed et al., *Morb. Mortal. Wkly. Rep.,* 58(14):362-5 (Apr. 17, 2009); Torrone et al., *Morb. Mortal. Wkly. Rep.,* 63(38):834-38 (Sep. 26, 2014). The most common clinical manifestations of *Chlamydia* infections are urethritis and epididymitis in males, and cervicitis and pelvic inflammatory disease (PID) in females. PID potentially leads to serious chronic long-term sequelae including ectopic pregnancy and infertility. See, Westrom et al., *J. Br. Fer. Soc.;* 1(1):23-30 (1996); Dunne et al., *Sex. Transm. Dis.,* 35(11 Suppl):S1-52 (November 2008); Schachter et al., *Curr. Opin. Infect. Dis.;* 15(5):491-5 (October 2002). In addition, *Chlamydia* infection increases the likelihood of human immunodeficiency virus (HIV) transmission and human papilloma virus (HPV)—induced neoplasia. See, Plummer et al., *J Infect. Dis.,* 163(2):233-9 (February 1991). Treatment with antibiotics is not efficient in preventing recurring infections, and such treatment interferes with development of natural immunity. See, Brunham et al., *J. Infect. Dis.,* 192(10):1836-44 (Nov. 15, 2005); Gotz et al., *Scand. J. Infect. Dis.,* 34(1):28-34 (2002). Further, antibiotic therapy against *Chlamydia* does not necessarily eradicate chronic infection or affect established pathology. See, Ou et al., *International Immunopharmacology,* 16: 505-513 (2013).

The *Chlamydia* major outer membrane protein (MOMP) is a vaccine candidate protein containing both B- and T-cell epitopes and that induces protective, cross-reactive immunity in animal models of immunization and genital/respiratory challenge with different *Chlamydia* serovars. See, Pal et al., *Infect. Immun.,* 73(12):8153-60, PMCID: PMC1307068 (December 2005); Pal et al., *Vaccine* 24(6):766-75 (Feb. 6, 2006); Kari et al., *J Immunol.,* 182(12):8063-70, PMCID: PMC2692073 (Jun. 15, 2009); Li et al., *Clin. Vaccine Immunol.,* 14(12):1537-44, PMCID:PMC2168373 (December 2007). MOMP is a trimeric porin with a 16-stranded β-barrel transmembrane core region with eight surface-exposed loops per each monomer, and containing four regions of sequence variability (variable domains or VDs) located within loops 2, 3, 5, and 6. See, Feher et al., *PLoS ONE,* 8(7): e68934, PMCID:PMC3723809 (2013); Sun et al., *J Bacteriol.,* 189(17):6222-35, PMCID:PMC1951919 (September 2007); Rodriguez-Maranon et al., *Protein Sci.,* 11(7):1854-61. PMCID:PMC2373662 (July 2002); Stephens et al., *J. Bacteriol.,* 169:3879-85 (1987); Peterson et al., *Infect. Immun.,* 59(11):4147-53, PMCID:PMC259009 (November 1991); Zhong et al., *Infect. Immun.,* 58(5):1450, PMCID:PMC258646 (May 1990). The VDs are highly immunogenic and elicit cross-serovar neutralizing monoclonal and polyclonal antibodies and T cell responses in animal and human models. See, Baehr et al., *Proc. Natl. Acad. Sci. U.S.A.,* 85(11):4000-4, PMCID:PMC280348 (June 1988); Ortiz et al., *Infect. Immun.,* 68(3):1719-23, PMCID: PMC97337 (March 2000); Farris et al., *Infect. Immun.,* 79(3):986-96, PMCID:PMC3067520 (March 2011); Pal et al., *Infection and Immunity,* 65(8): 3361-69 (1997). A single VD peptide as a vaccine has shown varying immunogenicity among mice of different haplotypes. See, Motin et al., *Clinical and Diagnostic Laboratory Immunology,* 6(3): 356-63 (1999).

Significant challenges in production and scale-up of this antigen exist for use of MOMP as a human *Chlamydia* vaccine. Purification of MOMP in native or recombinant form involve addition of detergents, has overall poor yields, and loses conformational epitopes during refolding. Scale up of an intracellular pathogen is not feasible for production. Vaccines using recombinant unfolded MOMP, MOMP peptides, or MOMP DNA-expressing plasmids have shown limited success. See, Pal et al., *Vaccine,* 24(6):766-75 (Feb. 6, 2006); Su et al., *Vaccine,* 13(11):1023-32 (August 1995); Pal et al., *Vaccine,* 15(5):575-82 (April 1997); Pal et al., *Vaccine,* 17(5):459-65 (Feb. 5, 1999); Shaw et al., *Infect. Immun.,* 70(3):1097-105, PMCID:PMC127771 (March 2002); Tifrea et al., *Vaccine,* 29(28):4623-31, PMCID: PMC3114171 (Jun. 20, 2011); Tifrea et al., *Infect. Immun.,* 81(5):1741-50, PMCID:PMC3648024 (May 2013); Schautteet et al., *Vaccine,* 29: 1399-1407 (2011). For example, MOMP peptides of a single variable domain have limited effectiveness among a variety of mice strains. See, Motin et al., *Clinical and Diagnostic Laboratory Immunology,* 6(3): 356-63 (May 1999).

*Chlamydia trachomatis* is the most common bacterial sexually transmitted infection worldwide with highest rates of infection, particularly in impoverished urban neighborhoods. See, Miller et al., *JAMA,* 291(18):2229-36 (May 4, 2004); Ahmed et al., *Morb. Mortal. Wkly. Rep.,* 58(14): 362-5 (Apr. 17, 2009); Torrone et al., *Morb. Mortal. Wkly. Rep.,* 63(38):834-38 (Sep. 26, 2014). Clinical manifestations of *Chlamydia* differ in males and females, and the infection is often asymptomatic in women. Long-term sequelae such as chronic abdominal pain, ectopic pregnancy, and infertility are of concern. See, Westrom, J. Br. Fer. Soc., 1(1):23-30 (1996); Dunne et al., *Sex. Transm. Dis.,* 35(11 Suppl):S1-S2 (November 2008); Schachter et al., *N. Engl. J. Med.,* 298 (8):428-35 (Feb. 23, 1978). Treatment with antibiotics does not prevent recurring infections, and reduces the off-set of high costs of medical treatments and interferes with development of natural immunity against the pathogen. See, Brunham et al., 0.1 Infect. Dis., 192(10):1836-44 (Nov. 15, 2005); Gotz et al., *Scand. J. Infect. Dis.,* 34(1):28-34 (2002).

As multidrug resistant strains of *Chlamydia* have emerged to decrease effectiveness of antibiotic treatment, a reliable and effective *Chlamydia* vaccine is urgently needed. See, Ou et al., *International Immunopharmacology,* 16: 505-513 (2013).

SUMMARY OF THE EMBODIMENTS

An aspect of the invention provides a composition for vaccinating a subject against an infection with *Chlamydia*, the composition comprising:

a recombinant *Neisseria* porin protein containing at least one antigenic variable domain of a surface protein of the *Chlamydia.*

The composition further includes in various embodiments at least one selected from the group consisting of: an adjuvant, a pharmaceutically acceptable buffer, a salt, and a carrier. In general, the antigenic variable domain is at least one portion of a *Chlamydia* major outer membrane protein (MOMP) selected from the group consisting of: SEQ ID NO: 11, SEQ ID NO: 12, SEQ ID NO: 13, and SEQ ID NO: 14. The antigenic variable domain of the *Chlamydia* MOMP is engineered to be displayed on an exposed surface of the recombinant protein. The recombinant protein is *Neisseria* PorB porin, and the antigenic variable domain is located on at least one loop of the *Neisseria* recombinant protein. These proteins from various species of each of *Neisseria* and *Chlamydia* generally have a typical protein β-barrel structure with exposed loops at the ends of the barrel strands, and the *Chlamydia* antigen is displayed on the recombinant *Neisseria* protein in the context of the loop. Accordingly, the recombinant protein has at least one of a secondary, tertiary, and quaternary structure conformation of a native *Neisseria* porin protein. The antigenic variable domain of the *Chlamydia* MOMP is a portion of at least one surface-exposed loop in the context of the original *Chlamydia* MOMP protein.

The composition the loop of the *Neisseria* recombinant protein is at least one selected from the group consisting of loops: 1 (SEQ ID NO: 3), 4 (SEQ ID NO: 6), 5 (SEQ ID NO: 7), 6 (SEQ ID NO: 8), 7 (SEQ ID NO: 9), and 8 (SEQ ID NO: 9). For example, the variable domain comprises an amino acid sequence selected from the group consisting of SEQ ID NOs: 11-14.

The composition *Neisseria* recombinant protein is in various alternative embodiments a porin protein from a species selected from the group consisting of: *Neisseria bacilliformis, N. cinerea, N. elongate, N. flavescens, N. lactamica, N. macacae, N. mucosa, N. polysaccharea, N. sicca, N. subflava, N. flava, N. gonorrhoeae*, and *N. meningitidis*. In further alternative embodiments the variable domain is from at least one *Chlamydia* species selected from the group consisting of: *Chlamydia trachomatis, C. pneumoniae, C. muridarum, C. caviae, C. abortus, C. pecorum, C. psittaci, C. pecorum, C. felis, C. avium* and *C. suis*. Many animal species suffer from chlamydial infections in captivity or even in the wild, including koalas, parrots and parakeets.

An aspect of the invention provides a method of making a vaccine for preventing or treating a subject for infection by a *Chlamydia* pathogen comprising:

engineering a nucleic acid construct encoding a recombinant protein of the vaccine by inserting an amino acid sequence encoding polynucleotide for at least one *Chlamydia* major outer membrane protein (MOMP) variable domain selected from the group consisting of: 1, 2, 3, and 4 (SEQ ID NO: 11-14) into a vector encoding a *Neisseria* recombinant protein, and transforming a cell of a standard protein expression species with the vector encoding the vaccine;

expressing in the cell the vaccine from the vector and isolating the recombinant protein; and, administering the vaccine to the subject thereby preventing or treating the infection. For example, the subject may be a high value farm animal, a high value zoo animal, a research animal, a human patient, or a healthy human in need of vaccination.

For example, in the method the cell is bacterial, the vector is an *Escherichia coli* plasmid and the cell is *E. coli*. The engineering step further includes inserting at least one *Chlamydia* MOMP variable domain amino acid sequence into a *Neisseria* PorB porin protein amino acid sequence at a position of the *Neisseria* protein which is a surface-exposed loop. The method further includes, after the expressing step, solubilizing the recombinant protein in detergent to form a solution or a micelle suspension, and further includes, after the solubilizing step, removing detergent from the solution.

An aspect of the invention herein provides a kit containing a composition for vaccinating a subject against a *Chlamydia* infection, the composition comprising all or a portion of a recombinant *Neisseria* porin protein containing at least one antigenic variable domain of a surface protein of the pathogen, the composition is in a unit dose and further comprises at least one selected from the group consisting of: an adjuvant, a pharmaceutically acceptable buffer, a salt, and a carrier. Various embodiments of the kit contain the adjuvant which is selected from at least one of the group consisting of: CpG oligonucleotides, CpG oligodeoxynucleotides, a water-in-oil emulsion, a monophosphoryl lipid A (MPLA), a squalene-in-water emulsion, an imidazoquinoline derivative, and a saponin. The antigenic variable domain of the composition in the kit is obtained from at least one *Chlamydia* major outer membrane protein (MOMP) selected from the group consisting of: SEQ ID NO: 11, SEQ ID NO: 12, SEQ ID NO: 13, and SEQ ID NO: 14. The recombinant protein of the composition of the kit is a *Neisseria* PorB porin.

BRIEF DESCRIPTIONS OF THE DRAWINGS

FIG. 1A shows the amino acid sequences of loops 2, 3, 5 and 6 of *C. trachomatis* mouse pneumonitis biovar (MoPn or *C. muridarum*) MOMP which contain the VD regions. The MoPn MOMP sequences are shown at sites of insertion into PorB sequences. PorB surface-exposed loop 1-8 amino acid sequences are underlined. The PorB residues selected as sites for MOMP loop insertion into PorB are indicated in boxes. Amino acid sequences are shown in Table 1.

FIG. 1B is a ribbon model of *N. lactamica* PorB trimer protein, showing loops 4, 5, 6 and 7 as L4, L5, L6 and L7, respectively.

FIG. 1C is a ribbon model of *N. lactamica* PorB trimer protein with MOMP loop 6/VD4 shown in FIG. 1A as inserted into PorB loop 4. Location of the inserted MOMP loop 6/VD4 is shown in the shaded rectangles.

Figure 1B:
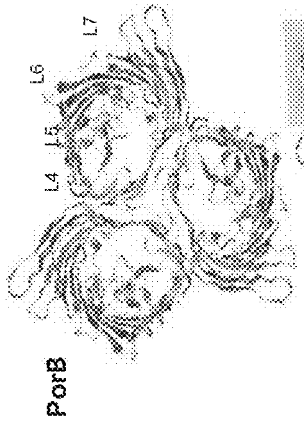
Figures 2A, 2B, 2C:
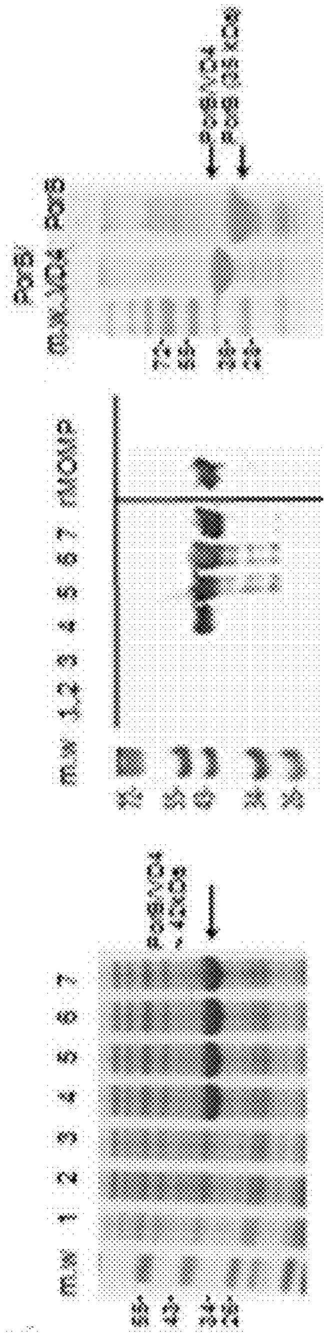
FIG. 2A is a photograph of a Coomassie stained SDS-PAGE analysis of a sample of PorB/VD4 expressed in cells of *E. coli* BL21. The results show PorB/VD4 presence at a molecular weight of approximately 42 kDA.
FIG. 2B is a photograph of a Western blot analysis of PorB/VD4 cell extracts blotted with anti-MOMP VD4 mAb. Recombinantly expressed MOMP (rMOMP) (lane 8) is the positive control.

FIG. 2C is a photograph of a Coomassie stained SDS-PAGE of samples of purified PorB/VD4 and PorB. PorB/VD4 was purified using an established chromatography method for production of Por B in detergent-free protein micelles. The purified PorB/VD4 monomer has a higher molecular weight than that of PorB because MOMP loop 6/VD4 (as shown in FIG. 1A) has been inserted.

Figure 3A:
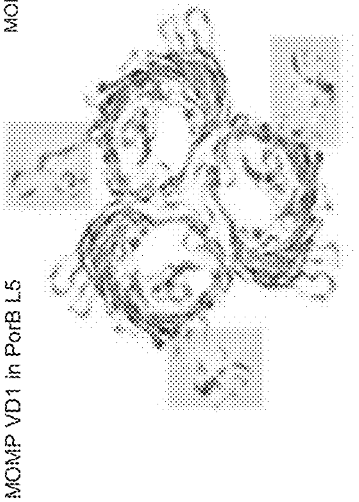

FIG. 3A is a ribbon model of PorB/VD1 trimer protein with MOMP VD1 inserted into PorB loop 5 (as shown in FIG. 1A). Location of the inserted MOMP loop 2/VD1 is shown in the shaded rectangles.

Figure 3B:

FIG. 3B is a ribbon model of PorB/VD2 trimer protein with MOMP VD2 inserted into PorB loop 6 (as shown in FIG. 1A). Location of the inserted MOMP loop 3/VD2 is shown in the shaded rectangles.

Figure 3C:

FIG. 3C is a ribbon model of PorB/VD3 trimer protein with MOMP VD3 inserted into PorB loop 7 (as shown in FIG. 1A). Location of the inserted MOMP loop 5/VD3 is shown in the shaded rectangles.

Figure 4:
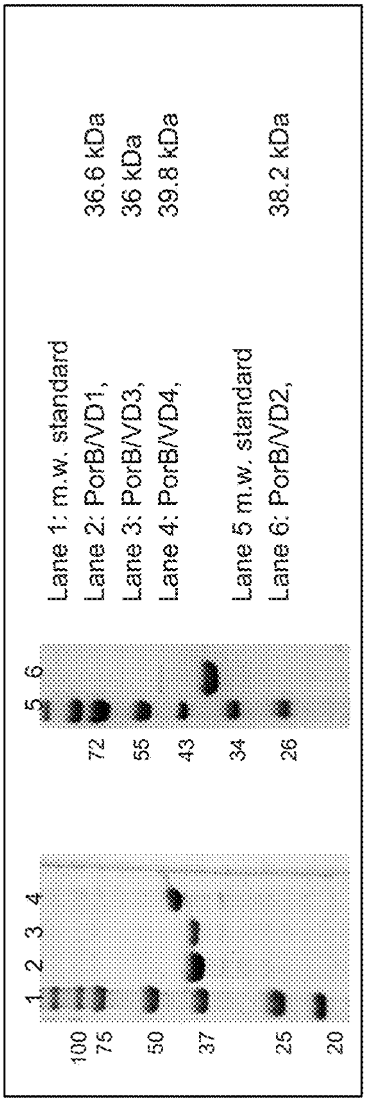

FIG. 4 is a photograph of a Coomassie stained SDS-PAGE of each of purified PorB/VD1, PorB/VD3, PorB/VD4 and PorB/VD2. Lane 2 contains purified PorB/VD1 (molecular weight of 36.6 kDA). Lane 3 contains purified PorB/VD3 (molecular weight of 36 kDA). Lane 4 contains purified. PorB/VD4 (molecular weight of 39.8 kDA). Lane 6 contains purified PorB/VD2 (molecular weight of 38.2 kDA). Molecular weight standards are shown in lanes 1 and 5

Figure 5:
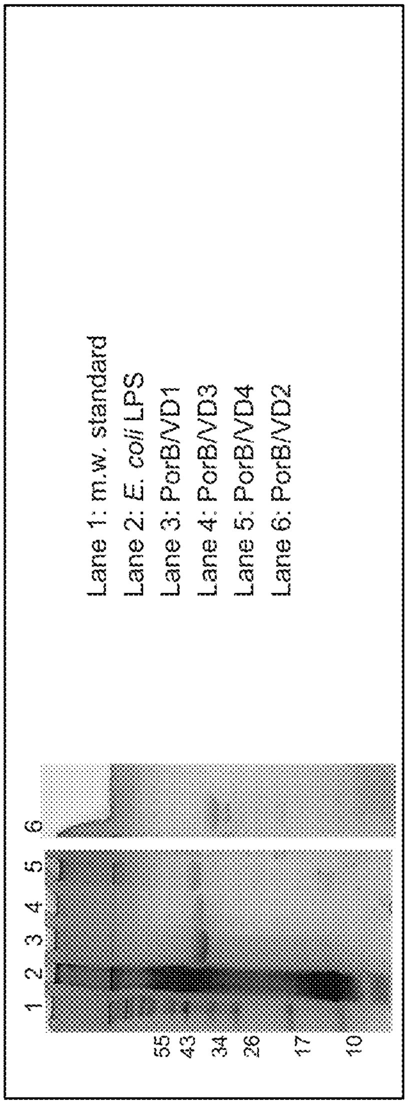

FIG. 5 is a photograph of a silver stained SDS-PAGE to test for LPS contamination of the purified proteins. Lane 1 contains molecular weight standards; lane 2 contains *E. coli* LPS; lane 3 contains PorB/VD1; lane 4 contains PorB/VD3; lane 5 contains PorB/VD4; and lane 6 contains PorB/VD2. The results show that LPS was not present and that the PorB/VD recombinant proteins migrated as bands at expected molecular weights as in FIG. 4.

Figure 6:
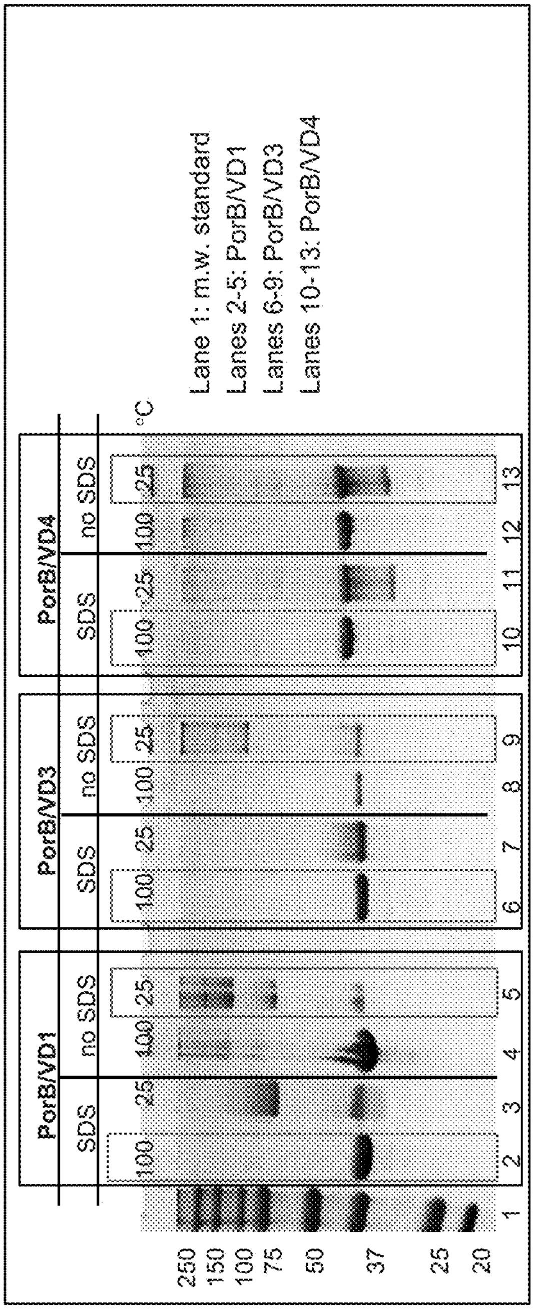

FIG. 6 is a photograph of a Coomassie stained non-denaturing SDS-PAGE of PorB/VD1, PorB/VD3 and PorB/VD4. Samples of PorB/VD hybrids were solubilized in sample buffer in the presence of SDS or in the absence of SDS, and were either thermally denatured at 100° C. or incubated at 25° C. for five minutes prior to electrophoresis on an SDS-free gel. Monomers of PorB/VD hybrids were detected in samples fully denatured in SDS at 100° C. in lanes 2, 6 and 10. Dimeric, trimeric and oligomeric forms were detected in non-denatured samples (no SDS, 25° C.) in lanes 5, 9 and 13 which showed a corresponding decrease in monomeric forms. Variable amounts of monomers, dimers and trimers were observed as a result of SDS denaturation and/or thermal denaturation (see lanes 3, 4, 11 and 12). Lane 1 contains molecular weight standards; lanes 2-5 show PorB/VD1 under different heat and reagent denaturing conditions; lanes 6-9 show PorB/VD3 under different heat and reagent denaturing conditions; and lanes 10-13 show PorB/VD4 under different heat and reagent denaturing conditions.

Figure 7:
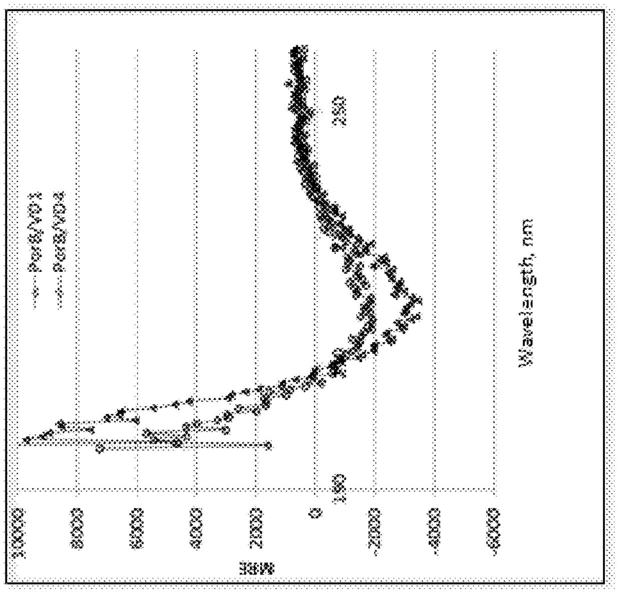

FIG. 7 is a plot of circular dichroism data for each of PorB/VD1 and PorB/VD4 to estimate secondary structure and spectral signature representative of the PorB β-barrel conformation. Each of the proteins shows the β-barrel conformation. The ordinate axis shows mean residue ellipticity (MRE) and the abscissa shows wavelength.

Figures 8A, 8B:
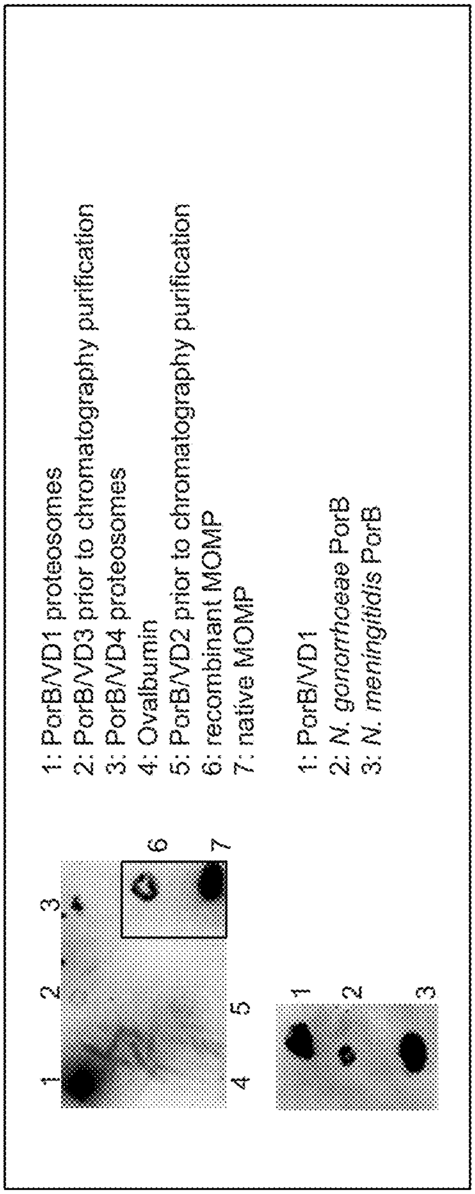

FIG. 8A is a photograph of dot blots. Purified PorB/VD1 and PorB/VD4 (dots 1 and 3, respectively), pre-chromatography samples of PorB/VD3 and PorB/VD2 (dots 2 and 5, respectively), purified recombinant MOMP and native MOMP (dots 6 and 7, respectively), and control ovalbumin (dot 4) were spotted (five μl each) on a PVDF membrane and were probed with anti-MOMP mAb. Dark spots indicate recognition of antigens by the anti-MOMP mAb. The results show that an anti-MOMP mAb cross-reacted with PorB/VD hybrids in dots 1 and 3 and to a lesser extent in dots 2 and 5 and that the anti-MOMP mAb clearly recognized both recombinant and native MOMP in dots 6 and 7, respectively.

FIG. 8B is a photograph of a dot blot. PorB/VD1, *N. gonorrhoeae* PorB and *N. meningitidis* PorB were spotted on a PVDF membrane in dots 1, 2 and 3, respectively, five μl each, and blotted with anti-*N. meningitidis* PorB polyclonal rabbit serum. The resulting dark spots at each dot show that anti-*N. meningitidis* PorB polyclonal rabbit serum recognized each of the samples.

FIGS. 9A-E are graphs of ELISA quantification of immunoglobulin (IgG) amounts produced in C57Bl/6 mice (4-6 weeks old) after subcutaneous injection of a composition containing purified PorB/VDs (10 μg/mouse) and adjuvants CpG DNA 1826 (10 μg/mouse) and Montanide ISA 720 (30:70 volume ratio). Control mice were injected with PBS. Anti-PorB/VD total IgG amounts were quantified by ELISA using plates coated with purified PorB/VDs or NL PorB (2 μg/ml, each plate). Bars marked indicate significant p-value as determined by one-way ANOVA with Tukey's multiple comparison test. Bars marked indicate a p-value less than or equal to 0.05 by unpaired t test with Welch's correction.

Figures 9A, 9B, 9C, 9D, 9E:
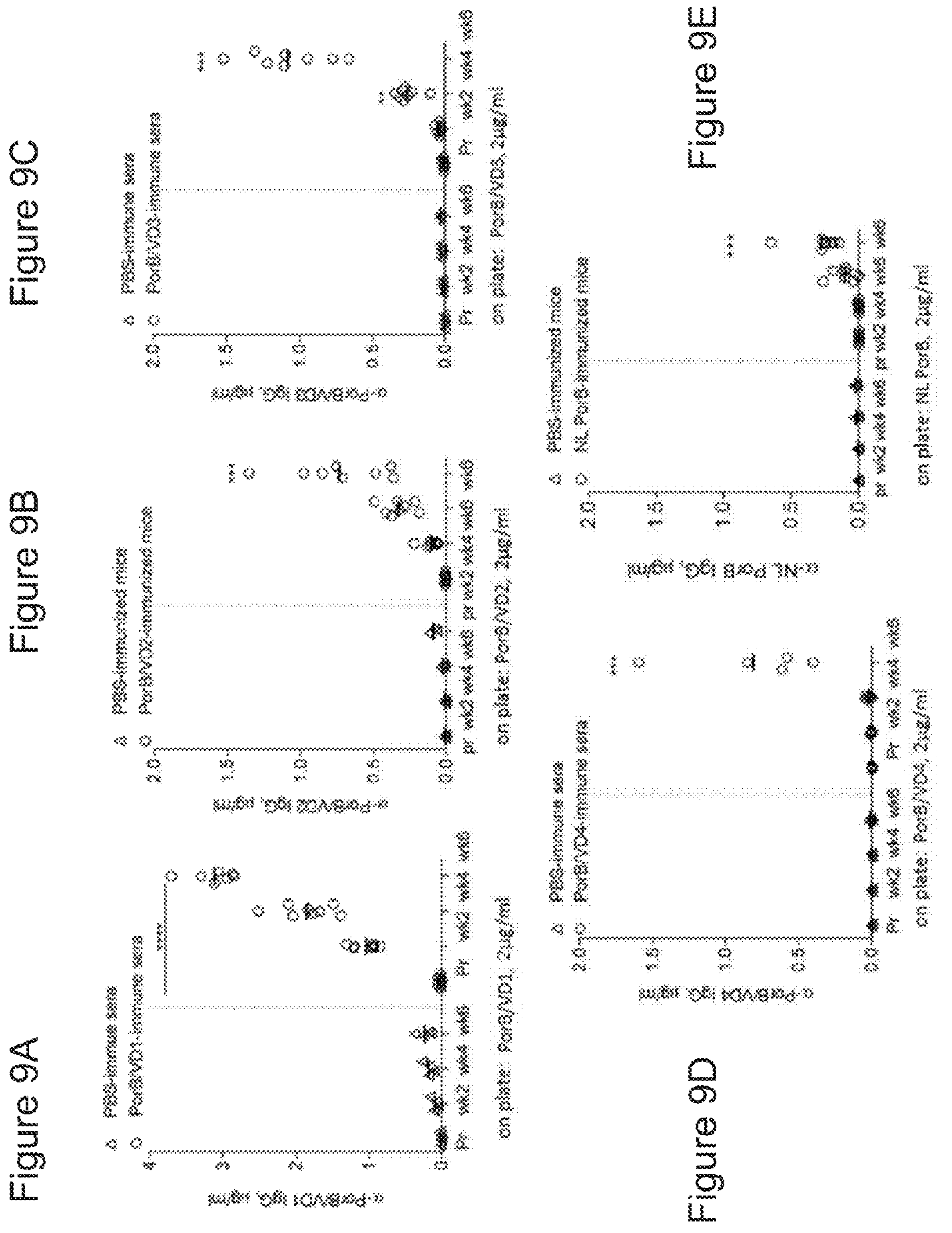

FIG. 9A shows a graph quantifying anti-PorB/VD1 IgG levels in mice either immunized with PorB/VD1 or control mice treated with PBS. Anti-PorB/VD1 IgG production increased to about 3.0 μg/ml in mice immunized with PorB/VD1 compared to mice treated with PBS control, in sera obtained at the week 6 time point after immunization. *** indicates a significant p-value determined by one way ANOVA with Tukey comparison test.

FIG. 9B shows a graph quantifying anti-PorB/VD2 IgG levels in mice either immunized with PorB/VD2 or control mice treated with PBS. The results show anti-PorB/VD2 IgG production increased to about 0.8 μg/ml in mice immunized with PorB/VD2 compared to mice treated with PBS control, in sera obtained at the week 6 time point after immunization. *** indicates a significant p-value determined by one way ANOVA with Tukey comparison test.

FIG. 9C shows a graph quantifying anti-PorB/VD3 IgG levels in mice either immunized with PorB/VD3 or control mice treated with PBS. The results show anti-PorB/VD3 IgG production increased to about 1.2 μg/ml in mice immunized with PorB/VD3 compared to mice treated with PBS, in sera obtained at the week 6 time point after immunizations. *** indicates a significant p-value determined by one way ANOVA with Tukey comparison test.

FIG. 9D shows a graph quantifying anti-PorB/VD4 IgG levels in mice either immunized with PorB/VD4 or control mice treated with PBS. The results show anti-PorB/VD4 IgG production increased to about 1.0 μg/ml in mice immunized with PorB/VD4 compared to mice treated with PBS control, in sera obtained at the week 6 time point after immunizations. *** indicates a significant p-value determined by one way ANOVA with Tukey comparison test.

FIG. 9E shows a graph quantifying anti-*Neisseria* lactamica indicated α- (anti-NL PorB) IgG levels in mice either immunized with NL PorB or control mice treated with PBS. The NL PorB was expressed recombinantly and purified. The results show anti-NL PorB IgG production increased to about 0.3 μg/ml in mice immunized with NL PorB compared to mice treated with PBS control, in sera obtained at the week 6 time point after immunizations. *** indicates a significant p-value determined by one way ANOVA with Tukey comparison test.

Figure 10A:
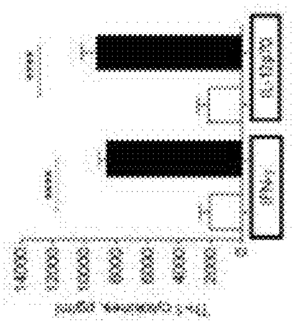
Figure 10B:
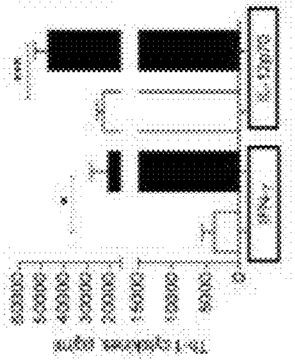
Figure 10C:
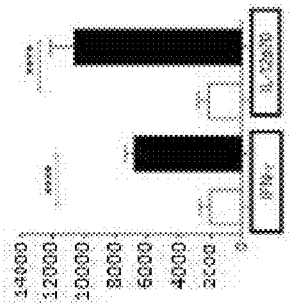
Figure 10D:
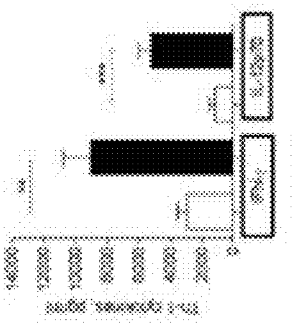
Figure 10E:
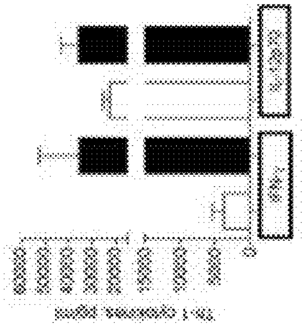
Figures 10F, 10G, 10H, 10I, 10J:
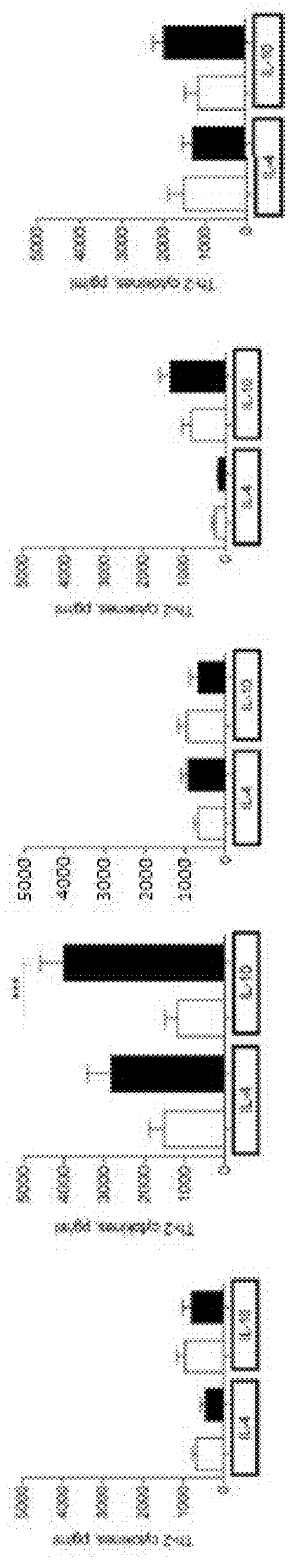
Figure 10K:
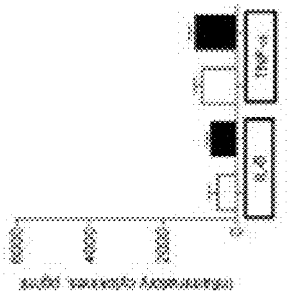
Figure 10L:
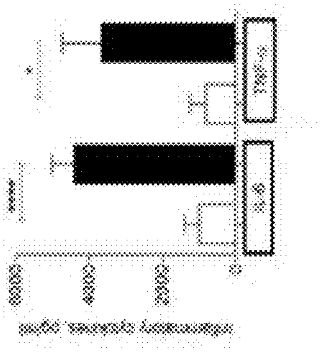
Figure 10M:
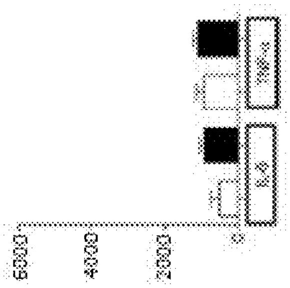
Figure 10N:
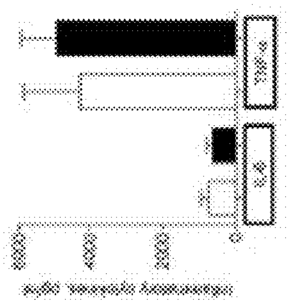
Figure 10O:
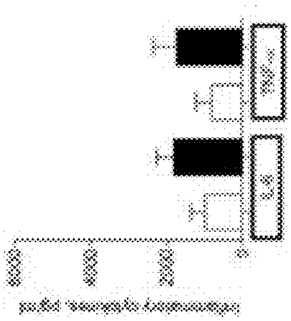

FIGS. 10A-10O are bar graphs of cytokine levels in the sera of the mice immunized subcutaneously with PorB/VD recombinant hybrid (solid bars), with NL PorB protein, or treated with control PBS (open bars). Analyzed samples were the same as those above in FIGS. 9A-E. Cytokine amounts are in picograms/milliliter (pg/ml), on the ordinate.

FIGS. 10A, 10F and 10K: immunization with PorB/VD1. The **** indicates a p-value<0.005 by unpaired t test with Welch's correction.

FIGS. 10B, 10G and 10L: immunization with PorB/VD2. The **, * and * indicate a p-value<0.05 by unpaired t test with Welch's correction.

FIGS. 10C, 10H and 10M: immunization with PorB/VD3. The **** and * indicate a p-value<0.005 by unpaired t test with Welch's correction.

FIGS. 10D, 10I and 10N: immunization with PorB/VD4. The * and  indicate a p-value=0.003 and 0.05, respectively, by unpaired t test with Welch's correction.

FIGS. 10E, 10J and 10O: immunization with NL PorB.

FIGS. 11A-E are graphs showing ELISA quantification of IgG subclasses of anti-PorB/VD antibodies in individual mouse sera using plates coated with purified PorB/VD antigens. Each of IgG1, IgG2b, IgG2c and IgG3 levels within the anti-PorB/VD sera from immunized mice were quantified. Pr indicates pooled pre-immune sera (stippled circle). *** indicates a significant p-value determined by one way ANOVA with Tukey comparison test. Pre-immune sera were combined for the assay, and each of the immune sera was tested individually. The amount of each IgG subclass in each individual mouse is compared to amount of each subclass in the pooled pre-immune serum pool.

Figure 11A:
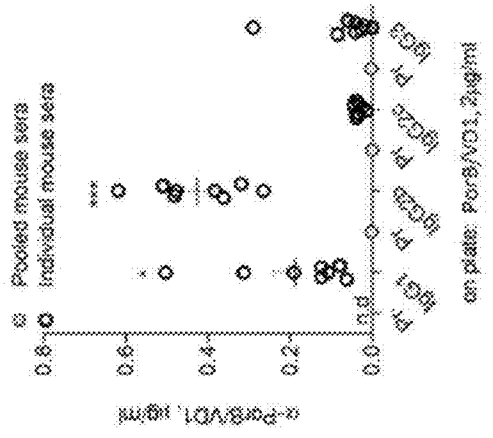
Figure 11B:
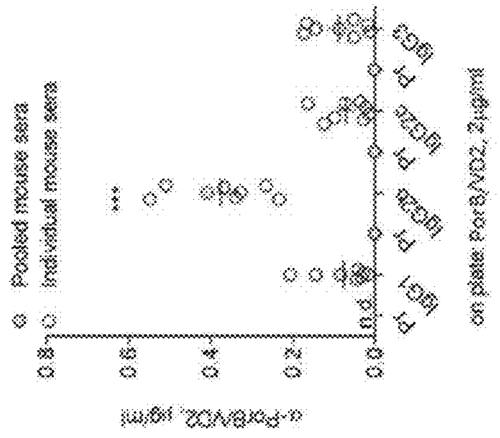
Figure 11C:
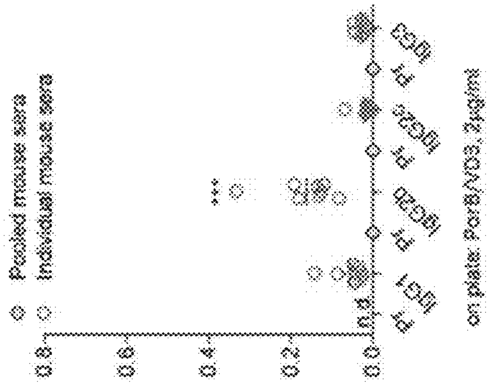
Figure 11D:
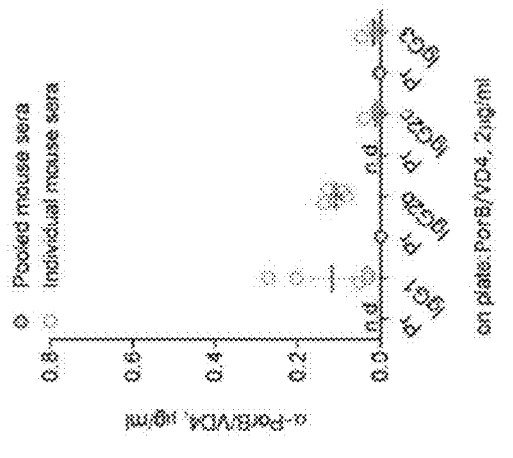
Figure 11E:
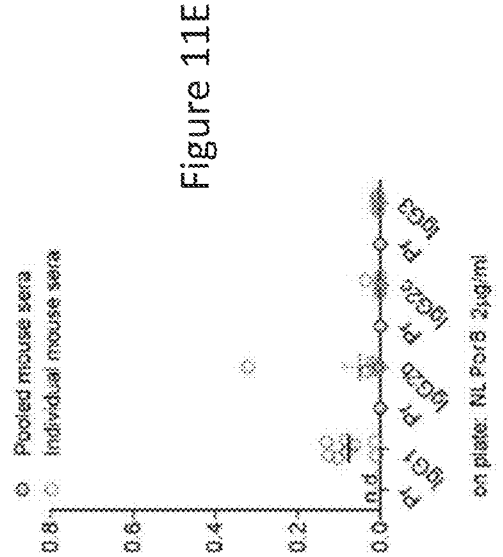

FIG. 11A: immunized with PorB/VD1;

FIG. 11B: immunized with PorB/VD2;

FIG. 11C: immunized with PorB/VD3;

FIG. 11D: immunized with PorB/VD4; and,

FIG. 11E: immunized with NL PorB.

The results show significantly increases primarily in IgG2b and in IgG1 sub-types of IgG for each construct.

Figure 12A:
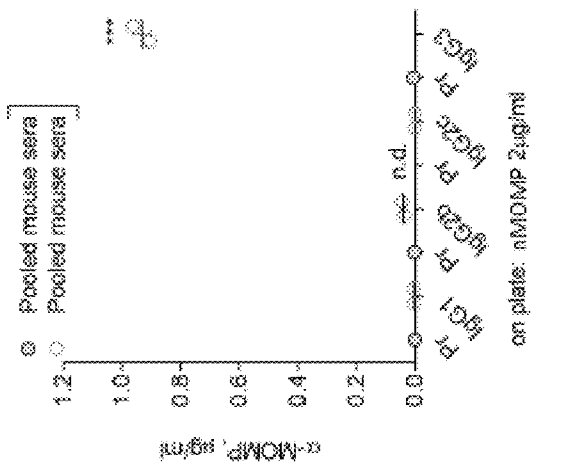

FIGS. 12A and B are graphs showing ELISA quantification of IgG subclasses of anti-MOMP antibodies from pooled mouse sera from mice immunized with MOMP and from pre-immune pooled mouse sera, using plates coated with 2 μg/ml native MOMP (nMOMP) or recombinant MOMP (rMOMP), respectively. Anti-MOMP IgG1, IgG2b, IgG2c and IgG3 levels were quantified in sera of immunized mice, and in pre-immune sera which is indicated as Pr. Pr indicates pooled pre-immune sera (stippled circle); open circles indicate sera from mice immunized with MOMP. Greater levels of anti-MOMP IgG3 than other subclasses of Ig G were observed on plates using nMOMP, and greater levels of IgG1, IgG2b and IgG3 were observed on plates using rMOMP. *** indicates a significant p-value determined by one way ANOVA with Tukey comparison test.

FIG. 13A-C are graphs analyzing IgG cross-reactivity of anti-PorB/VD sera to NL PorB, anti-PorB/VD sera to nMOMP, and anti-MOMP to PorB/VDs, respectively by ELISA quantification of IgG levels.

FIG. 13A shows ELISA quantification of sera for the amounts of anti-PorB/VD1, anti-PorB/VD2, anti-PorB/VD3, anti-PorB/VD4, and anti-NL PorB, each analyzed on plate with 2 μg/ml NL PorB. The results show that the anti-PorB/VD sera were observed to have cross reacted with antigen NL PorB. NL PorB is the PorB porin from *N. lactamica* (the carrier protein) expressed recombinantly and purified. Symbols for the serum samples in the graph data set on the abscissa from left to right follow the symbols listed in the legend from top to bottom.

FIG. 13B shows ELISA quantification of anti-PorB/VD IgG amounts in each of pre-immune pools, and in sera of anti-PorB/VD1, anti-PorB/VD2, anti-PorB/VD3, anti-PorB/VD4, anti-NL PorB and anti-MOMP, each analyzed on a plate with 2 μg/ml nMOMP. The results show about a 50 to 100-fold increase in anti-PorB/VD IgG concentrations in the sera of mice immunized against MOMP. *** indicates a significant p-value determined by one way ANOVA with Tukey comparison test. Symbols for the serum samples in the graph data set on the abscissa from left to right follow the symbols listed in the legend from top to bottom.

FIG. 13C shows ELISA quantification measuring IgG cross-reactivity of anti-MOMP activity from immunized mice to plates each with 2 μg/ml PorB/VD2, PorB/VD3, PorB/VD4, NL PorB and nMOMP, respectively. These data show about 50 to 150 fold increase in anti-MOMP activity levels in sera which cross-reacted with antigens on the plate. Large and specific increases were observed in MOMP IgG activity in mice immunized with MOMP compared to much lower induction of anti-MOMP IgGs in mice immunized with the PorB/VD constructs or with NL PorB. Symbols for the serum samples in the graph data set on the abscissa from left to right follow the symbols listed in the legend from top to bottom.

Figure 14:
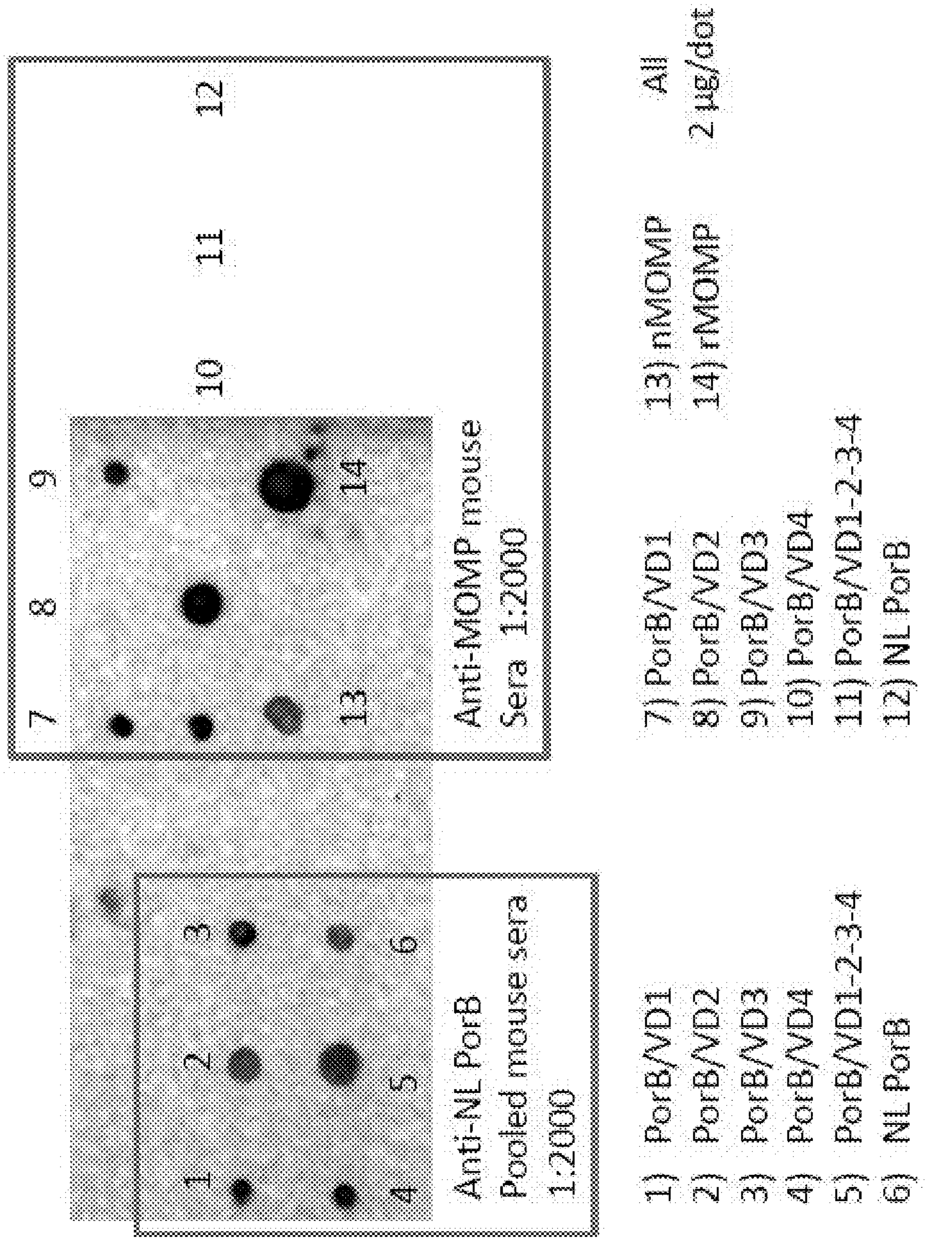

FIG. 14 is a photograph of a dot blot on a PVDF nitrocellulose membrane of anti-NL PorB pooled mouse sera and anti-MOMP pooled mouse sera which is visualized by blotting with antibodies to measure cross-reactivity of anti-NL PorB and anti-MOMP antibodies to PorB/VDs. The results on the left show that anti-NL PorB sera cross-reacted with each of PorB/VD1, PorB/VD2, PorB/VD3, PorB/VD4, PorB/VD1-2-3-4 and NL PorB antibodies which shows the presence of each type of antibody or presence of cross-reacting proteins in the pooled anti-NL PorB mouse sera.

DETAILED DESCRIPTION

Live and inactivated whole organism-based vaccines induce protection from *Chlamydia* challenge in both humans and non-human primates. See, Greenwood et al., *Biochem. J.,* 89:114-22 (1963); Longbottom et al., *Vet. J.,* 171(2):263-75 (March 2006); Grayston et al., *Sex. Transm. Dis.,* 5(2): 73-7 (April 1978); MacDonald et al., *J. Infect. Dis.,* 149(3): 439-42 (March 1984); Wang et al., *Am. J. Ophthalmol.,* 63(5): Suppl-45 (May 1967). The immune response is short-lived, serovar/subgroup-specific protective immunity that causes hypersensitivity reactions to exacerbate disease during subsequent infection episodes due to pathologic reactions to chlamydial antigens. See, Brunham et al, *Nat. Rev. Immunol.,* 5(2):149-61 (February 2005); Zhang et al., *Journal of Infectious Diseases,* 176: 1035-40 (1997); Boje et al., *Immunology and Cell Biology,* 94: 185-195 (2016).

*Chlamydia* MOMP is a candidate for locating appropriate sources of antigen for a subunit vaccine. Monoclonal antibodies against the VD regions have neutralizing activity in vitro and in vivo, and epitopes within the VDs are recognized by T cells, resulting in T-cell mediated immunity against the intracellular pathogen. See, Su et al., *J. Exp. Med.,* 172:203-12 (1990); Nunes et al., *PLoS ONE,* 5(10), PMCID:PMC2950151 (2010); Ortiz et al., *Infect. Immun.,* 68(3):1719-23, PMCID:PMC97337 (March 2000). MOMP VDs are unique for each serovar; therefore, specific anti-VD antibodies provide broad coverage against all infecting strains. Immunization of mice with native MOMP (nMOMP) purified from the *C. trachomatis* mouse pneumonitis biovar (formerly MoPn; now named *Chlamydia muridarum*) has been shown to induce protection against genital and respiratory challenge. See, Farris et al., *Infect. Immun.,* 79(3):986-96, PMCID:PMC3067520 (March 2011); Pal et al., *Infect. Immun.,* 62(8):3354-62, PMCID:PMC302966 (August 1994); Pal et al., *Infect. Immun.,* 72(7):4210-6, PMCID:PMC427456 (July 2004); Cheng et al., *Microbes. Infect.,* 16(3):244-52, PMCID:PMC3965591 (March 2014); Tifrea et al., *Microbes. Infect.,* 15(13):920-7, PMCID:PMC3842390 (November 2013). A recombinant protein vaccine containing four polymorphic membrane proteins of *Chlamydia* identified to induce a $CD4^+$ T cell reaction in a subject has been shown to elicit a more robust immune response than the same membrane administered individually. See, Yu et al., *Vaccine,* 32(36): 4672-80 (2014).

Development of MOMP as a vaccine antigen for humans has encountered major issues including: preparation of nMOMP because the protein is highly hydrophobic with low solubility which requires detergents for purification; scaling-up manufacture of nMOMP because the protein extracted from intracellular-growing *Chlamydia* organisms; and, failure of recombinant MOMP (rMOMP) to refold due to its hydrophobic and cysteine-rich nature leading to quick degradation, and reducing antigenicity in vivo. Attempts in the past to use rMOMP, MOMP peptides, or DNA plasmids expressing MOMP had only limited success. See, Dong-Ji et al., *Infect. Immun.,* 8(6):3074-8, PMCID:PMC97534 (June 2000); Su et al., *J. Exp. Med.,* 175(1):227-35, PMCID: PMC2119084 (Jan. 1, 1992); Igietseme et al., *Infect. Immun.,* 68(12):6798-806, PMCID:PMC97783 (December 2000); Pal et al., *Vaccine,* 17(5):459-65 (Feb. 5, 1999); Pal et al., *Vaccine,* 24(6):766-75 (Feb. 6, 2006). Recent platforms for use of rMOMP include synthetic multi-epitope antigens, inclusion in protein micelles (proteosomes), and delivery vectors such as nanoparticles, gas vesicles, and expression in transgenic carrots and rice. See, Tu et al., *Acta Biochim. Biophys. Sin.* (Shanghai) (Mar. 28, 2014); Singh et al., *Vaccine,* 24(8): 1213-24 (Feb. 20, 2006); Tifrea et al., *Microbes. Infect.,* 15(13):920-7, PMCID:PMC3842390 (November 2013); Massari et al., *Infect. Immun.,* 81(1):303-10, PMCID:PMC3536141 (January 2013); Singh et al., *Vaccine,* 24(8):1213-24 (Feb. 20, 2006); Zhu et al., *Appl. Microbiol. Biotechnol.,* 98(9):4107-17 (May 2014); Fairley et al., *Int. J Nanomedicine,* 8:2085-99, PMCID: PMC3682632 (2013); Dixit et al., *Nanomedicine* (Mar. 4, 2014); Cambridge et al., *Int. J. Nanomedicine,* 8:1759-71, PMCID:PMC3656902 (2013); Childs et al., *Vaccine,* 30(41):5942-8 (Sep. 7, 2012); Kalbina et al., *Protein Expr. Purif,* 80(2):194-202 (December 2011); Zhang et al., *Vaccine,* 31(4):698-703 (Jan. 11, 2013).

MOMP has been demonstrated to be a *Chlamydia* vaccine candidate antigen as shown by data observed in vitro and in vivo in various animal models. Anti-MOMP polyclonal and monoclonal antibodies against the VDs have neutralizing activity in genital and respiratory challenge with different *Chlamydia* serovars. See, Pal et al., *Vaccine,* 24(6):766-75 (Feb. 6, 2006); Kari et al., *J. Immunol.,* 182(12):8063-70, PMCID:PMC2692073 (Jun. 15, 2009); Li et al., *Clin. Vaccine Immunol.,* 14(12):1537-44, PMCID:PMC2168373 (December 2004). Immune defenses against *Chlamydia* also require $CD4^+$ T-cell mediated responses for pathogen clearance. See, Su et al., *Vaccine,* 13(11):1023-32 (August 1995); Olsen et al., *J. Infect. Dis.* (Mar. 6, 2015). Subunit and protein-based acellular vaccines require addition of adjuvants to enhance specific humoral immunity. Adjuvants are generally chose that favor T-helper cell differentiation. See, Toussi et al., *Vaccines,* 2(2):323-53 (2014). Bacterial products or derivatives recognized by toll-like receptors (TLRs) have immune adjuvant activity and drive distinct Th1, Th2, or Th17-type responses. TLR9 ligands typically induce Th1-type immunity favoring dendritic cell (DC) activation, release of Th1-type cytokines IL-12 and IFN-γ, and production of IgG2a in mice and IgG3 in humans. Ibid. Many different adjuvants have been administered with MOMP through various immunization routes. Mucosal and systemic vaccination with MOMP and a combination of CpG DNA (TLR9 ligand) and Montanide (water-in-oil emulsion) induces a strong Th1 protective response against *Chlamydia* respiratory and genital challenge and secretion of high levels of MOMP-specific IgG2a antibodies in mice. See, Pal et al., *Infect. Immun.,* 70(9):4812-7, PMCID:PMC128273 (September 2002); Farris et al., *Infect. Immun.,* 78(10):4374-83, PMCID:PMC2950360 (October 2010); Carmichael et al., *Vaccine,* 29(32):5276-83, PMCID:PMC3139009 (Jul. 18, 2011); Ralli-Jain et al., *Vaccine,* 28(48):7659-66, PMCID: PMC2981640 (Nov. 10, 2010); Pal et al., *Vaccine,* 24(6): 766-75 (Feb. 6, 2006); Pal et al., *Vaccine,* 15(5):575-82 (April 1997); Cheng et al., *Microbes. Infect.,* 16(3):244-52. PMCID:PMC3965591 (March 2014). Alternatively, cholera toxin, tetanus toxin, hepatitis virus, human papillomavirus, or derivatives thereof have been used also as adjuvants. See, O'Meara et al., *PLoS One,* 8(4): e61962 (2013); Andrew et al., *Journal of Reproductive Immunology,* 91: 9-16 (2011); Taylor et al., *Investigative Ophthalmology & Visual Science,* 29(12): 1847 (1988); Xu et al., *Vaccine,* 29: 2672-78 (2011). CpG DNA 1826 and Montanide ISA 720 are being analyzed for use in human trials and are potentially relevant for development of a human *Chlamydia* vaccine. See, Klinman et al., *Int. Rev. Immunol.,* 25(3-4):135-54 (May 2006); Miles et al., *Vaccine,* 23(19):2530-39 (Mar. 31, 2005). Prior to the present application, a vaccine composition containing MOMP fused to Hepatitis B virus core antigen showed potential as a subunit vaccine for *Chlamydia*. See, Jiang et al., *Oncotarget,* 6(41): 43281-92 (2013).

Embodiments of the present invention contain a vaccine composition having recombinant *Neisseria* porin with at least one antigenic variable domain of a *Chlamydia* MOMP. The variable domains are inserted into the *Neisseria* porin at positions resulting in expression on the surface of the recombinant protein.

Previously, a variable domain of MOMP was inserted in a neutralization antigenic site of poliovirus to form a recombinant vaccine. See, Murdin et al., *Infection and Immunity,* 61(10): 4406-14 (1993).

Figure 1C:
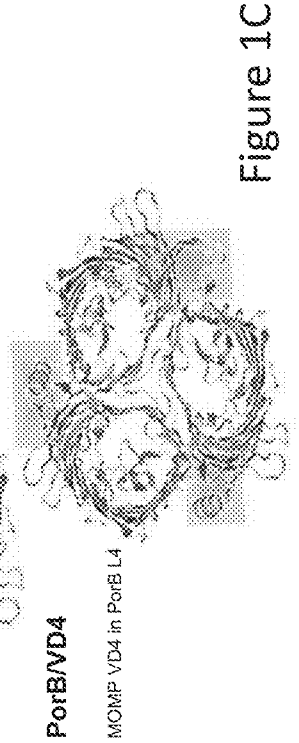

Example 1 summarizes the scientific rationale and design considerations for making the embodiments of the compositions. Example 2 discusses primary sequence and other structural characterizations of antigenic variable domains for loop swapping of *Chlamydia* MOMP inserted into a recombinant *Neisseria* porin. FIG. 1A contains amino acid sequences of MOMP loops 2, 3, 5, and 6 with the amino acid residues that form the variable domains (VDs) in gray. For clarity, sequences are listed in Table 1. FIG. 1B is a ribbon model of native *Neisseria* lactamica PorB trimer with loops 4-7 labeled. FIG. 1C is a ribbon model of recombinant *N. lactamica* PorB containing MOMP VD4 at PorB loop 4. FIGS. 2A and 2B are photographs of SDS-PAGE and Western blot analysis, respectively, of recombinant PorB/VD4 clones. FIG. 2C is a photograph of SDS-PAGE analysis comparing sizes of components of native PorB and recombinant PorB/VD4.

Example 3 describes expression and purification of recombinant hybrid proteins with VD immunogenic regions of MOMP inserted into surface-exposed loops of PorB, and a method of chromatography purification and analysis of the PorB/VD recombinant proteins. Example 4 examines structural features of the recombinant proteins by SDS-PAGE and Western blot. FIGS. 3A-3C are ribbon models of PorB/VD1, PorB/VD2, and PorB/VD3, respectively. Example 5 describes methods of analyzing the higher structural integrity of PorB/VD recombinant proteins using electrophoresis and circular dichroism. Example 6 describes vaccination techniques for immunization of mice, ELISA analysis, and statistical analysis of the recombinant proteins. Examples 7 and 8 describes a method of determining immune recognition by anti-MOMP and anti-PorB antibodies. Example 9 describes anti-PorB/VD and anti-NL PorB antibody production in mice immunized with each of PorB/VD1, PorB/VD2, PorB/VD3, PorB/VD4 and NL PorB. Example 10 describes effect of immunizations on cytokine levels and concomitant association with immune responses. Example 11 shows total amounts of antibody production in sera with respect to different subclasses of IgG types. Example 12 describes cross reactions of sera of mice immunized with PorB/VD and NL PorB proteins described herein with antigen NL PorB. Example 13 describes immunization with the proteins described herein in the context of animal immune responses and considerations for human immunizations particular to the protein antigens and sexually transmitted diseases described herein.

Pharmaceutical Compositions

In one aspect of the present invention, pharmaceutical compositions are provided, which contain at least one or more variable domains of *Chlamydia* major outer membrane protein (MOMP) inserted into at least one surface-exposed loop of *Neisseria* porB porin protein. The compositions optionally further comprise a pharmaceutically acceptable buffer, adjuvant or a carrier. In certain embodiments the composition is encapsulated or micro-encapsulated. In certain embodiments, these compositions optionally further comprise one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. (Remington: *The Science and Practice of Pharmacy,* 22nd Edition, by Pharmaceutical Press, 2013) describes various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; and phosphate buffer solutions, as well as other non-toxic compatible lubricants such as sodium lauryl sulfate and magnesium stearate, as well as coloring agents, releasing agents, coating agents, preservatives and antioxidants can also be present in the composition, according to the judgment of the formulator.

Therapeutically Effective Dose

In yet another aspect, according to the methods of treatment of the present invention, sexually transmitted diseases are presented by administering the pharmaceutical composition, as described herein. Thus, the invention provides methods for the treatment of a sexually transmitted disease associated with *Chlamydia* comprising administering a therapeutically effective amount of a pharmaceutical composition comprising active agents that include at least one disease antigen engineered into a *Neisseria* porB protein, in such amounts and for such time as is necessary to achieve the desired result. It will be appreciated that this encompasses administering an inventive pharmaceutical as a therapeutic measure to prevent onset of the bacterial or viral infection or prevent further development of the infection, or as a prophylactic measure to inhibit or prevent or treat the bacterial or viral infection.

In certain embodiments of the present invention a "therapeutically effective amount" of the pharmaceutical composition is that amount effective for eliciting sufficient immune response for preventing further development of a bacterial or viral infection. The compositions, according to the method of the present invention, may be administered using any amount and any route of administration effective for prevention of development and/or treatment of infection. Thus, the expression "amount effective for prevention of infection", as used herein, refers to a sufficient amount of composition to prevent or retard development of the target pathogen species such as *Chlamydia* cells, and even cause regression of or recovery from an onset of the previously acquired infection. The exact dosage is chosen by the individual physician in view of the patient to be treated. Dosage and administration are adjusted to provide sufficient levels of the active antigen or to maintain the desired effect of eliciting an immune response. Additional factors which may be taken into account include the severity of the disease state, e.g., symptoms of infection; age, weight and gender of the patient; diet, time and frequency of administration; drug combinations; reaction sensitivities; and tolerance/response to therapy. Long acting pharmaceutical compositions might be administered every 3 to 4 days, every week, or once every two weeks depending on half-life and clearance rate of the particular composition. It is within the bounds of the particular invention that successful treatment may require only a single dose.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total single or more frequent one or more booster injections of the compositions of the present invention will be decided by the attending physician within the scope of sound medical judgment. For any active agent, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of active agent which ameliorates the symptoms or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. The data obtained from cell culture assays and animal studies are used in formulating a range of dosage for human use.

The effective dose is expressed as micrograms or milligrams of protein as measured in a laboratory. It is within the knowledge of an attending physician to determine tolerance and requirement, based on prior exposure of the subject to infection by the sexually transmitted disease.

Administration of Pharmaceutical Compositions

After formulation with an appropriate pharmaceutically acceptable carrier in a desired dosage, the pharmaceutical compositions of this invention can be administered to humans and other mammals topically (as by powders, ointments, or drops), orally, intravenously, subcutaneously, rectally, parenterally, intracisternally, intravaginally, intraperitoneally, bucally, ocularly, or nasally, depending on the severity and location of the exposure to patients having active infections, and to the strain of the sexually transmitted disease being treated.

Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl carbonate, ethyl acetate, benzyl benzoate, oils (in particular, cottonseed, groundnut, corn, germ, olive, castor, and sesame oils), polyethylene glycols and fatty acid esters of sorbitan, and mixtures thereof. Besides inert diluents, the oral compositions can also include adjuvants such as wetting agents, emulsifying and suspending agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous infections may be treated with aqueous drops, a mist, an emulsion, or a cream. Administration may be therapeutic or it may be prophylactic. Prophylactic formulations may be present or applied to the site of potential infection, for example to mucous membranes of genitalia. The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms or forms for oral administration are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable and oral formulations are also prepared by entrapping the agent in liposomes or microemulsions which are compatible with body tissues.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Adjuvants suitable for administration with the compositions described herein include, but are not limited to, $C_pG$ oligonucleotides including ODN1826 (InvivGen, San Diego, Calif.), $C_pG$ oligodeoxynucleotides, $C_pG$ oligodeoxyribonucleotides, water-in-oil emulsions including Montanide™ ISA 51 and Montanide™ ISA 720, polyethoxylated sorbitan esters, monoesters, and triesters of lauric, stearate, or oleic fatty acids, aluminum gels or salts, such as aluminum hydroxide, aluminum phosphate, and aluminum potassium sulfate, monophosphoryl lipid A, complete Freund's adjuvant, incomplete Freund's adjuvant, squalene-in-water emulsion such as MF59, squalene such as AS03, a purified plant extract such as QS-21, Risi's adjuvant, Titermax and Specol.

Uses of Pharmaceutical Compositions

As discussed and described in greater detail in the Examples herein, a pharmaceutical composition containing all or a portion of a recombinant *Neisseria* porin protein containing at least one antigenic variable domain of a *Chlamydia* MOMP protein is administered as a vaccine to treat or prevent *Chlamydia* infection. Vaccination can be prophylactic, i.e. given to asymptomatic or pre-symptomatic subjects, or can be administered to patients suffering with the infection.

It will be appreciated that the diagnostic, prognostic and therapeutic methods encompassed by the present invention are not limited to treating conditions in humans, but may be used to treat similar conditions in any mammal including but not limited to bovine, canine, feline, caprine, ovine, porcine, murine, avian and equine species.

EXAMPLES OF EMBODIMENTS

Example 1. Design Considerations

An embodiment of the invention provides methods of development of a suitable antigen for engineering into a vaccine composition to protect a subject against infection by a *Chlamydia*. Engineered MOMP antigens that eliminate the shortcomings of the native and recombinant *Chlamydia* MOMP proteins were generated. Analysis of the structure and function features of MOMP antigens guide selection to obtain those for subsequent analysis of immunogenicity. *Neisseria* PorB/VD antigens were used in combination with adjuvants that specifically favor Th1 cytokine responses in vivo, which are known to act against *Chlamydia*. Adjuvants are key elements for stimulating long-term humoral and cell-mediated immune responses to specific antigen in protein subunit vaccines and their use is known in the context of animal immunizations with MOMP proteins.

Feasibility to assess induction of specific immune responses in mice to the novel antigens and fulfill unmet requirements for the use of MOMP was assessed as shown in Examples herein. Effective combinations of VDs were selected for expression into PorB for the purpose of using a mouse model of immunization and challenge with the *C. muridarum* model. Induction of humoral and cell-mediated immune responses elicited by these novel antigens is to be correlated with protection from *Chlamydia* in trials with genital challenge and infection. Compositions of PorB/VD antigens provided herein include VDs from the major sexually-transmitted human *C. trachomatis* serovars (D through K), in different combinations, for a broad protection against this pathogen in humans. Furthermore, due to the trimeric nature of the carrier protein (PorB) and to the interchangeability of the VDs into the PorB loops, selected VDs were designed and were expressed at multiple (triple) copy number, thus constructing a super-antigen. A recombinant subunit vaccine engineered to efficiently deliver MOMP VDs for immune recognition is accordingly provided herein.

Example 2. Construction of Recombinant Hybrid Proteins with VD Immunogenic Regions of MOMP Inserted into Surface-Exposed Loops of PorB By sequence analysis of *Chlamydia* MOMP proteins and *Neisseria* PorB, regions suitable for loop swapping were identified. Constructs for expression of MOMP VDs into surface-exposed loops of PorB in *E. coli* were generated. The resulting recombinant PorB/VD antigens were purified and examined for folding and structural features by biochemical methods. A structural characterization of novel recombinant antigens for inclusion into a subunit vaccine against *Chlamydia* is thereby provided. See Table 1, which is a listing of amino acid sequences SEQ ID NO: 1-14 used in the Examples described herein. Structures of insertions are shown in the amino acid sequence in FIG. 1A.

TABLE 1

| Sequences and SEQ ID numbers |
|---|
| SEQ ID NO: 1 - *Neisseria* PorB amino acid sequence<br>MKKSLIALTLAALPVAAMADVTLYGTIKAGVETYRTVKHTDGKVTEVKTG<br>SEIADFGSKIGFKGQEDLGNGLKAIWQLEQNASIAGTDSGWGNKQSFIGL<br>KGGFGTVRAGNLNSILKSTGDNVNAWESGKATEDVLQVSKIGAPEHRYAS<br>VRYDSPEFAGFSGSVQYAPKDNSG-KNGESYHVGLNYQNSGFFAQYAGLF<br>QRHGEGTKATVGEPVEKLQVHRLVGGYDNDALYASVAVQQQDAKLTDASN<br>SHNSQTEVAATVAYRFGNVTPRVSYAHGFKGTVAKADGDNTYDQVVVGAE<br>YDFSKRTSALVSAGWLQEGKGAGKTVSTASTVGLRHKF |
| SEQ ID NO: 2 - recombinant *Neisseria* PorB amino acid sequence containing variable domains 2, 3, 5, and 6 of *Chlamydia* MOMP<br>MKKSLIALTLAALPVAAMADVTLYGTIKAGVETYRTVKHTDGKVTEVKTG<br>SEIADFGSKIGFKGQEDLGNGLKAIWQLEQNASIAGTDSGWGNKQSFIGL<br>KGGFGTVRAGNLNSILKSTGDNVNAWESGKATEDVLQVSKIGAPEHRYAS<br>VRYDSPEFAGFSGSVQYKWSRASFDADTIRIAQPKLETSILKMTTWNPTI<br>SGSGIDVDTKYHVGLNYQNSGFFAQYAGLFQRVLKTDVNKQFEMGAAPTG<br>DADLTTAPTPASRENPAYGKHMQVHRLVGGYDNDALYASVAVQQQLGATS<br>GYLKGNSAAFNLVGLFGRDETAVAADDIPNVSLSQAATVAYRFGNVTPRV<br>SYAHGAEFTINKPKGYVGQEFPLNIKAGTVSATDTKDASIDYQVVVGAEY<br>DFSKRTSALVSAGWLQEGKGAGKTVSTASTVGLRHKF |
| SEQ ID NO: 3 - Loop 1<br>AGVETYRTVKHTDGKVTEVKTGSEIADF |
| SEQ ID NO: 4 - Loop 2<br>NASIAGTDSGWGNKQ |
| SEQ ID NO: 5 - Loop 3<br>DNVNAWESGKATEDVLQVSKIGAPEHRY |
| SEQ ID NO: 6- Loop 4<br>APKDNSGKN |
| SEQ ID NO: 7 - Loop 5<br>RHGEGTKATVGEPVEKLQ |
| SEQ ID NO: 8 - Loop 6<br>DAKLTDASNSHNSQTEV |
| SEQ ID NO: 9- Loop 7<br>FKGTVAKADGDNTYD |
| SEQ ID NO: 10 - Loop 8<br>QEGKGAGKTVST |
| SEQ ID NO: 11 - VD1<br>AAPTGDADLTTAPTPASR |
| SEQ ID NO: 12 - VD2<br>VGLFGRDETAVAADDIPN |
| SEQ ID NO: 13 - VD3<br>VGQEFPLNIK |
| SEQ ID NO: 14 - VD4<br>MTTWNPTISGSGIDVD |

MOMP is a surface protein and constitutes approximately 60% of the total outer membrane proteins of *Chlamydia* (Caldwell H D, et al. *Infect. Immun.* 1981 March; 31(3): 1161-76). Molecular characterization of MOMP has identified four serovar-specific variable domains (VDs) within the regions that protrude from the bacterial surface, which account for the immunogenicity of this protein and induction of protective immunity (Ortiz et al., *Infect. Immun.* 2000 March; 68(3):1719-23. PMCID:PMC97337; Pal et al., *Vaccine,* 1997 April; 15(5):575-82; Zhong et al., 1990 May; 58(5):1450-5. PMCID:PMC258646; Pal et al., *Infect. Immun.* 2001 October; 69(10):6240-7. PMCID:PMC98757). As an intrinsic membrane protein, MOMP has low water solubility and limited stability in vitro. In prior attempts, purification of MOMP was carried out in the presence of detergents, and disadvantages were observed to be due to destabilizing effects on protein structures, inactivation of function, and toxicity in vitro and in vivo.

Therefore, detergent-solubilized proteins cannot be used to perform immunological assays or as vaccine candidates in humans. Attempts to alleviate the problems in production and use of MOMP as a recombinant vaccine antigen have had scarce success. A strategy was explored herein for presentation of the VDs for immune recognition by inserting the VDs into a carrier protein.

The *C. trachomatis* mouse pneumonitis biovar (also designated MoPn or *C. muridarum*) strain was used because a murine *Chlamydia* genital challenge model is available for testing. Similar to human *C. trachomatis* strains, MoPn MOMP has four VD regions which elicit serovar cross-reactive protective antibodies in mice against genital and respiratory challenges with *Chlamydia* MoPn (Pal et al., *Infect. Immun.* 2005 December; 73(12):8153-60. PMCID: PMC1307068; Farris et al., *Infect. Immun.* 2011 March; 79(3):986-96. PMCID:PMC3067520; Tifrea et al., *Microbes. Infect.* 2013 November; 15(13):920-7. PMCID: PMC3842390). The PorB porin protein from the human commensal organism *N. lactamica* was used as an exposed surface protein for display of the antigens (Toussi et al., *Infect. Immun.* 2012 October; 80(10):3417-28. PMCID: PMC3457564; Liu et al., *Infect. Immun.* 2010 December; 78(12):5314-23. PMCID:PMC2981301). MOMP and PorB share major topology and function similarities, including a β-barrel trimeric structure with several surface-exposed loops and TLR2-dependent activity, which is an important pathway in immune recognition. In particular, TLR2 signaling by PorB is dependent on its folded, trimeric conformation, which can provide a potential system for screening structure/function features of the PorB/VD hybrids constructed here (Kattner et al., *J. Struct. Biol.* 2014; 185(3): 440-447; Massari et al., *J. Immunol.* 2002 Feb. 15; 168(4): 1533-7; Massari et al., *Infect. Immun.* 2013 January; 81(1): 303-10. PMCID:PMC3536141; Massari et al., *Protein Expr. Purif.* 2005 December; 44(2):136-46; Toussi et al. 2012, Ibid).

By sequence analysis of MOMP and PorB, common residues in the surface-exposed loops of these proteins were identified for genetic manipulation (FIG. 1A). The sequence of MOMP loops 2, 3, 5 and 6 (gray rectangles) containing the VD regions (light letters inside shaded rectangles) is shown applied to the PorB sequence. The surface-exposed loops 1, 4, 5, 6, 7 and 8 of PorB are underlined and bold; loops 2 and 3 (pore region) are underlined. The residues selected for MOMP loop insertion into PorB are indicated. FIG. 1B shows structure modeling and surface charge analysis of *N. lactamica* PorB trimer, and the position of loops 4, 5, 6 and 7, and C. FIG. 1C shows PorB/VD4, with MOMP loop 6/VD4 location into PorB loop 4 (shaded areas). Positive-charged residues are identified using SWISS-MODEL (Biasini et al., *Nucleic Acids Res.* 2014 July; 42 (Web Server issue):W252-W258. PMCID:PMC4086089; Arnold et al., *Bioinformatics.* 2006 Jan. 15; 22(2):195-201). Mutagenesis was used to identify loops 4 through 7 of PorB, which are located away from the trimeric interface and are thus unlikely to destabilize trimer formation (FIG. 1B).

The entire loop 6 of MoPn MOMP was cloned into the loop 4 of PorB and inserted into the serovar-specific, highly immunogenic VD4 region into PorB (PorB/VD4; FIG. 1A; Peterson et al. 1991, Ibid.; Ortiz et al., 2000; Ibid.; Su et al. *Vaccine* 1993; 11(11):1159-66; Kim et al., *Curr. Opin. Immunol.* 2001 August; 13(4):429-36; cloning provided by GenScript, Piscataway, N.J.). *E. coli* expressing the PorB/VD constructs were cloned in pET17 plasmid (by GenScript). PCR products were generated containing PorB DNA sequences upstream and downstream of loop 4, and containing the VD4 region of MOMP with primers containing PorB sequences in the 5' ends. The PCR products were joined by overlapping PCR, cloned into a TA PCR vector and were sequenced, and were then cloned in an expression vector in *E. coli* BL21 (DE3) as previously described (Madico et al., *J. Immunol.* 2007 Apr. 1; 178(7):4489-97). Based on the crystal structure of *N. meningitidis* PorB (PDB:3WI4_A; 75% sequence identity with *N. lactamica* PorB, (Kattner et al. 2014, Ibid.), the structure of the resulting PorB/VD4, was modeled and is shown in FIG. 1C.

Example 3. Expression and Purification of Recombinant Hybrid Proteins with VD Immunogenic Regions of MOMP Inserted into Surface-Exposed Loops of PorB Constructs for the expression of *N. lactamica* PorB in *E. coli* were made. A set of *E. coli* strains expressing each of the PorB/VD constructs each cloned in plasmid pET17 was obtained (GenScript). A PorB hybrid for each of individual VD of VD1, VD2, VD3 and VD4, and combined VD hybrids having two, three or four variable domains (indicated VD1-2, VD1-3, VD1-4, VD2-3, VD2-4, VD3-4, VD1-2-3, VD1-2-4, VD1-3-4, VD2-3-4, VD1-2-3-4) were constructed and expressed in *E. coli* as described herein.

For experiments, cells of each clone were inoculated into 10 ml of LB broth containing 50 μg/ml carbenicillin overnight at 37° C. with shaking, then expanded into 200 ml of broth and grown overnight. The next day, 0.2 mM of IPTG was added and the culture was grown for further 3-4 hours. Bacteria were centrifuged at 5,000 rpm at 4° C. for 15 minutes and the pellet was weighed and resuspended in 3 ml of TEN buffer (50 mM Tris-HCl, 1 mM EDTA, 100 mM NaCl [pH 8.0]) per gram (wet weight), followed by addition of 8 μl of phenylmethylsulfonylfluoride (PMSF) (50 mM stock solution in anhydrous ethanol) and 80 μl of lysozyme (stock solution 10 mg/ml) per gram of cells, mixed at r.t. for 20 minutes and addition of 4 mg deoxycholate per gram of cells. The solution was placed at 37° C. and mixed until viscous, then 20 μl of DNase I (stock solution 1 mg/ml) per gram of cells was used to lyse DNA at r.t. The solution was centrifuged at 12,000 rpm for 15 minutes at 4° C. ant the pellet was resuspended in 5 ml TEN buffer containing 0.1 mM PMSF and 8 M urea, sonicated in a bath sonicator followed by addition of 5 ml of 10% (wt/vol) Zwittergent 3-14.

PorB/VDs hybrid proteins were purified by established methods as described herein and examined by Western blot with monoclonal anti-MOMP VDs antibodies (Baehr et al., *Proc. Natl. Acad. Sci. U.S.A* 1988 June; 85(11):4000-4. PMCID:PMC280348; Pal et al., *Vaccine* 1997 April; 15(5): 575-82). The protein suspension was loaded to two ion-exchange columns in tandem: a DEAE Sepharose CL-6B (Amersham) column and a CM-Sepharose (Amersham) column (2.5×10 cm, Econo column; Bio-Rad, Hercules, Calif., USA) at a flow rate of 1.8 ml/min. The columns were washed with buffer containing 50 mM Tris, 10 mM EDTA, 0.05% Zwittergent 3-14, and 0.02% azide, pH 8.0 (washing buffer), until the 280 nm absorbance returned to baseline and the flow through was collected. The proteins in the flow through were precipitated with ethanol (80% v/v, final concentration), resuspended in buffer containing 100 mM Tris, 10 mM EDTA, 0.2 M NaCl, 0.05% Zwittergent, and 0.02% azide, pH 8.0, and subjected to gel-filtration chromatography on a Sephacryl S-300 (Amersham) column (2.6×180 cm) at a flow rate of 0.25 ml/min. The porin-containing fractions identified by Coomassie stain of SDS-PAGE were collected and precipitated with ethanol (80% v/v). The precipitate was resuspended in loading buffer at pH 7.5, and loaded on a Matrex Cellufine Sulfate (Millipore, Billerica, Mass., USA) column (2.5×10 cm, Econo column) at a flow rate of 6 ml/min. The column was washed with washing buffer at pH 7.5, and a linear gradient of 0.2-0.5 M NaCl was applied. The porin-containing fractions, eluted between 0.24 and 0.4 M NaCl, were detected as above. The proteins were precipitated with ethanol as above and resuspended in 1 ml of 10% d-octyl-glucoside (DOG) in 10 mM Hepes, pH 7.2, followed by extensive dialysis ($>5\times10^{10}$ times the original volume of the sample in 36 h) against PBS containing 0.02% sodium azide for removal of the detergent and formation of the porin proteosomes. Absence of *E. coli* LPS contamination was assessed by silver staining of SDS-PAGE and by *Limulus* amoebacyte assay as shown in the Examples herein. Correct folding and trimeric structure of PorB/VD hybrids was assessed by gel electrophoresis and by circular dichroism (CD) (Massari et al. 2005 Ibid.).

Example 4. PorB/VD Analysis by SDS-PAGE and Western Blot

Production of PorB/VD4 in clones were examined by Coomassie stained SDS-PAGE (FIG. 2A) and by Western blot with an anti-MOMP VD4 mAb (FIG. 2B; Pal et al, Mid). PorB/VD4 was purified using chromatography for production of PorB in detergent-free protein micelles (proteasomes; Massari et al. 2005 Ibid.).

The purified PorB/VD4 monomer was observed to have a higher molecular weight than that of PorB as expected due to the insertion of loop 6 of MOMP (FIG. 2C). This monomer was further observed to be recognized by the L21-10mAb against VD4 epitopes common to 15 *C. trachomatis* serovars and MoPn (Baehr et al. 1988 Ibid.; Zhang et al., *J. Immunol.* 1987 Jan. 15; 138(2):575-81). Recombinant MOMP from *C. trachomatis* was included in the analysis as a positive control.

These results show that PorB/VD hybrid proteins suitable for production of high amounts of detergent-free, folded, immunoreactive MOMP antigens were obtained.

Example 5. PorB/VDs Structural Features and Cytokine Induction after Immunizations Methods for purification and production of neisserial porins in detergent-free, nanoparticle-like, stable and immunogenic structures called proteasomes are described herein (Massari et al. 2005, Ibid. and Kattner et al., *Appl. Biochem. Biotechnol.* 2015 March; 175(6): 2907-15). Modeling of the PorB/VD4 structure (FIGS. 1A-C) and that of other PorB/VD single hybrids (FIGS. 3A-C) was used to visualize the position of MOMP VD1, VD2 and VD3 as having been inserted into PorB loops. The modelling data of MOMP VDs inserted into the extracellular loops of PorB, and indicates that the PorB β-barrel core structure was not affected by insertions, and that monomer folding and trimer formation was not compromised. Surface changes were displayed for each of PorB/VD1 (FIG. 3A), PorB/VD2 (FIG. 3B) and PorB/VD3 (FIG. 3C) using SWISS-MODEL (Biasini et al. 2014, Ibid; Arnold et al. 2006 Ibid). MOMP loops/VD locations are shown in the shaded rectangular areas.

PorB/VD hybrid structures were observed by the biochemical methods of electrophoresis (see FIGS. 4-6) and CD (See FIG. 7). The extent of PorB/VDs folding and trimer formation that could be correlated with cell activation in vitro as a result of TLR2 signaling was determined. These functions depend on the correct trimeric conformation of PorB (Massari et al. 2005, Ibid.). PorB and PorB/VD4 were determined to induce comparable IL-8 secretion in the TLR2-overexpression HEK cell model. Without being limited by any particular theory or mechanism of action, it is believed that some PorB/VD hybrids fail to trimerize because of steric interference from the MOMP loops, and that the individual monomers are correctly folded and the VDs efficiently presented for immune recognition in vivo. Since there are numerous residues common with the sequences of MOMP loops and PorB loops and there are several PorB variants with variable-length loops, the cloning strategy accommodates the VDs in different combinations based on the PorB loop flexibility to obtain structurally correct trimers that display the antigen for immune recognition.

Example 6. Vaccination with PorB/VD Antigens and Humoral and Cell Mediated Immune Responses MOMP is a prime *Chlamydia* vaccine candidate antigen, shown in vitro and in vivo in various animal models. Anti-MOMP polyclonal and monoclonal antibodies against the VDs have neutralizing activity in genital and respiratory with different *Chlamydia* serovars (Pal et al. 2005 Ibid.; Pal et al. 2006, Ibid; Kari et al. 2009, Ibid.; Li et al. 2007, Ibid.). Immune defenses against *Chlamydia* also require CD4+ T-cell mediated responses for pathogen clearance (Su et al. 1995, Ibid.; Olsen et al. 2015, Ibid.). Subunit and protein-based acellular vaccines require addition of immune adjuvants to enhance specific humoral immunity which favor T-helper cell differentiation (Toussi et al. 2014, Ibid.). Mucosal and systemic vaccination with MOMP and a combination of CpG DNA 1826, which is a TLR9 ligand, and Montanide ISA 720, which is an water-in-oil emulsion, has been a successful combination for inducing a strong Th1 protective response against *Chlamydia* respiratory and genital challenge and secretion of high levels of MOMP-specific antibodies in mice (Pal et al. 2006, Ibid.; Pal et al. *Vaccine.* 1997, Ibid.; Cheng et al. 2014, Ibid.; Pal et al. 2002, Ibid.; Farris et al. 2010, Ibid.; Carmichael et al. 2011, Ibid.; Ralli-Jain et al. 2010, Ibid.). CpG DNA 1826 (Klinman D M, 2006 Ibid.) and Montanide ISA 720 (Miles et al. 2005, Ibid.) are candidates for use in humans and are used herein as adjuvants for immunization of mice as a pre-clinical test of the MOMP VD construct, prior to development of a human *Chlamydia* vaccine.

Groups of ten mice were immunized to each antigen to account for mouse-to-mouse immune response variation to allow statistical evaluation by the non-parametric Wilcoxon rank assay. C57Bl/6 mice were injected subcutaneously with PorB/VD antigens combined with CpG DNA and Montanide ISA 720. C57Bl/6 mice (4-6 weeks old) were injected subcutaneously with purified PorB/VDs (10 μg/mouse) combined with CpG DNA 1826 (10 μg/mouse) and Montanide ISA 720 (30:70 volume ratio; Pal eta 1.2005, Ibid.) or were treated with PBS as a control. Pre-immune sera and immune sera were collected after each of three immunizations at two weeks apart (days 14, 28 and 42) and stored at −20° C. until analysis. Anti-PorB/VD total IgGs were quantified by ELISA using plates coated with purified PorB/VDs (2 μg/ml) as previously described for PorB (Liu X, et al. *Vaccine* 2008 Feb. 6; 26(6):786-96) or with purified nMOMP (2 μg/ml) as a positive control. Production was measured by ELISA of anti-MOMP VD-specific antibodies (total IgG and IgG subclasses) and of Th1-type cytokines (IL-12p70 and IFN-γ), Th2-type cytokines (IL-4, IL-10), and inflammatory cytokines (TNF-α and IL-6) in the sera of immunized mice.

Whether some VDs are more immunogenic than others or whether changes in the PorB loop structure and conformation are conferred by the different VDs that may favor or reduce immunogenicity is evaluated. Mice (C57Bl/6, 4-6 weeks old; Jackson Laboratory, Bar Harbor, Me.) were housed and cared for in accordance with National Institutes of Health (NIH) and Tufts University IACUC protocols. Individual PorB/VD antigen (each of PorB/VD1, PorB/VD2, PorB/VD3, or PorB/VD4, n=4, for each antigen) and combined PorB/VD hybrids were used. As a negative control, mice (n=10) were injected with PBS. Pre-immune sera were collected at day 0 prior to initial injections. Mice were vaccinated three times at two week intervals and immune sera were collected two weeks after each immunization at days 14, 28 and 42, respectively. Collected sera samples were stored at −20° C. for subsequent analysis.

Example 7. Methods of Analysis of Anti-Chlamydial Antibody in Collected Immune Sera Production in sera of immunized mice: anti-MOMP VD-specific antibodies total IgG and IgG subclasses and Th-1 and Th-2-type cytokines IL-2, IFN-γ, IL-4, IL-10, TNF-α and IL-6 were analyzed. PorB/VD hybrids plus CpG DNA and Montanide ISA 720 were used to immunize mice and assess induction of innate and adaptive host immune responses.

For analysis of antibody production, 96-well plates (Immulon) were coated with 2 μg/ml of purified proteins in carbonate buffer pH 9.6 at 4° C. for 24 h, washed three times with PBS/0.05% Tween-20 followed by 1 h blocking with 5% BSA in PBS at room temperature. Serial dilution of individual mouse sera were incubated at 4° C. for 24 h washed and incubated with a secondary anti-mouse IgG alkaline-phosphatase (AP) conjugated antibody (Sigma) for 2 h at room temperature followed by detection with one step PNPP substrate (Pierce) as specified by the manufacturer. The absorbance was measured at O.D. 405 nm. To quantify the amount of anti-porin serum IgG in μg/ml, a reference standard curve was used. A plate was coated with 10 μg/ml of a goat anti-mouse IgG F(ab') 2-specific antibody (Jackson Laboratories), incubated with serial dilutions of a known amount of mouse total IgG (Sigma) followed by secondary antibody and detection as described. The amount of anti-porin serum IgG was extrapolated from the standard curve using a linear regression function.

Production of total IgG and IgG subclasses to each of the VDs was measured by ELISA in the sera collected from immunized mice. For analysis, plates were coated with protein from PorB/VD hybrid clones (2 μg/ml) (Bhasin et al., *Infect. Immun.* 2001 August; 69(8):5031-6) or with Cm-MOMP 25-mer overlapping peptides (10 μg/ml) specific for the VD regions (Tifrea et al. 2013, Ibid) to determine B-cell epitope recognition by antibodies present in collected serum. Cytokines were measured in the sera by ELISA using commercially available cytokine ELISA kits per the manufacturer's specification (R&D Systems, Minneapolis, Minn.).

ELISA assays (FIGS. 9A-E, 10A-O, 11A-E, 12A-B and 13A-C) were performed in triplicate and each triplicate was repeated to assess reproducibility. Statistical analysis of each data set was performed using PRISM (Graphpad, Inc., La Jolla, Calif.) to determine normal distribution, mean, geometric mean, standard deviation and standard error. Comparative statistical analyses were examined and based on the normality of the data, parametric and non-parametric tests were performed using t test or ANOVA to assess antibody production in immunized mice populations. The data are discussed in examples herein.

Example 8. Recognition by Anti-MOMP Antibody and Anti-PorB

Immune recognition of the PorB/VDs by a monoclonal antibody specific for purified MOMP (Baehr W, et al. *Proc. Natl. Acad. Sci. U.S.A* 1988 June; 85(11):4000-4; Pal S, et al. *Vaccine* 1997 April; 15(5):575-82) was assessed by dot blot and Western blotting. Purified PorB/VD1 and PorB/VD4 (FIG. 8A, dots 1 and 3, respectively), PorB/VD3 and PorB/VD2 (5 μl pre-chromatography samples; dots 2 and 5, respectively), purified recombinant MOMP and native MOMP (dots 6 and 7, respectively) and negative control ovalbumin (dot 4) were spotted on a PVDF membrane. The dots were observed to be recognized by the anti-MOMP mAb, except for negative control ovalbumin. Since the purified proteins have a much higher concentration/volume ratio than the samples prior to chromatography, variability in the dots intensity was expected.

PorB/VDs were also examined using a polyclonal rabbit serum specific for *N. meningitidis* PorB to assess immune recognition of the PorB component. A representative dot blot of candidate protein PorB/VD1 is shown in FIG. 8B, dot 1, as were purified PorB from *N. gonorrhoeae* and *N. meningitidis* (FIG. 8B, dots 2 and 3). Immune recognition of purified PorB/VDs, including PorB/VD1/VD2/VD3/VD4, and NL PorB was further observed by dot blot with the same antibodies.

Example 9 Production of Antibodies and Analysis of Antibody Activities

Mice were immunized with PorB/VD recombinant proteins and NL PorB, and data was collected at specific time points and antibody amounts were quantified by ELISA as described in examples herein. Production of specific anti-PorB/VD and NL PorB total IgG levels (FIG. 9A-E, n=8 mice, open circle) was detected as a function of time and was compared to each of pre-immune sera and sera from mice immunized with PBS. Production of specific antibodies for each of the constructs with PorB/VD1, PorB/VD2, PorB/VD3, PorB/VD4 and NL PorB were observed in FIGS. 9A-9E, respectively. Greatest level of antibody production was observed with immunization with PorB/VD1.

These data indicate that each construct was immunogenic and elicited a robust immune response in the subjects by six weeks after the initial immunization injection. Thus a vaccine combining two or more antigens for *Chlamydia* might be a potential preventive vaccine for variable strains found in the population, among human pathogens or pathogens for animals.

Antibody production by mice immunized with PorB/VD1 was observed and compared to control mice injected with PBS, as shown in FIG. 9A. Antibody titer achieved was about 3-4 μg/ml anti-PorB/VD1. Similarly, FIG. 9B shows that mice immunized with PorB/VD2 produced an increase of almost 1 μg/ml anti-PorB/VD2 antibody concentration in sera collected at the week 6 time point; FIG. 9C shows that mice immunized with PorB/VD3 produced an increase of between 1.0 and 1.5 μg/ml anti-PorB/VD3 antibody concentration in sera collected at the week 6 time point; and FIG. 9D shows that mice immunized with PorB/VD4 produced an increase of almost 1.0 μg/ml anti-PorB/VD4 antibody concentration in sera collected at the week 6 time point. Further, mice immunized with NL PorB increased anti-NL PorB antibody concentrations to about 0.5 μg/ml in sera collected at the week 6 time point, see FIG. 9E.

These results show that immunization of mice with PorB/VD recombinant proteins induced increased production of cognate antibodies for each of the recombinants analyzed, with most production detected at the week 6 time point. Because antibodies against the VD regions have neutralizing activity in vitro and in vivo and epitopes within the VDs are recognized by T-cells, resulting in T-cell mediated immunity, immunization with PorB/VD recombinants shows a mechanism to vaccinate against *Chlamydia* infecting strains. See, Su et al., *J. Exp. Med.,* 172:203-12 (1990); Nunes et al., *PLoS ONE,* 5(10), PMCID:PMC2950151 (2010); Ortiz et al., *Infect. Immun.,* 68(3):1719-23, PMCID:PMC97337 (March 2000).

Example 10. Cytokine Production in Immunized Subjects

The levels of each of Th1 cytokines IL-12p70 and IFN-γ, Th2 cytokines IL-4 and IL-10, and inflammatory cytokines TNF-α and IL-6 were measured in sera of mice immunized with each of the constructs described herein in a composition with adjuvants CpG DNA and Montanide ISA 720. Data is shown in FIGS. 10A-O.

The cytokine data in FIGS. 10A-E for immunization with each of the PorB/VD hybrid proteins and NL PorB were evidence that robust increases in production of Th1 cytokines IFN-γ and IL-12p70 were induced in mice immunized with the respective antigens. Immunization of mice with PorB/VD1 induced an increase in IL-12p70 production about four fold and IFN-γ production about four-fold compared to control mice as shown in FIG. 10A. Immunization with PorB/VD2 induced an increase in IFN-γ production about five fold and IL-12p70 production about two fold compared to mice treated with PBS (FIG. 10B). Immunization of mice with PorB/VD3 induced an increase in IFN-γ production about 3.5 fold and IL-12p70 production about 4.5 fold compared to control (FIG. 10C). Immunization of mice with PorB/VD4 induced an increase in IFN-γ production about three fold and IL-12p70 production about five fold compared to control. Immunization with NL PorB induced an increase in IFN-γ production about nine fold and IL-12p70 production about 1.5 fold compared to control (FIG. 10E).

Further, immunization of mice only with PorB/VD2 induced production of Th2 cytokines IL-4 and IL-10. See, FIG. 10G. In contrast, immunization with PorB/VD1, PorB/VD3, PorB/VD4 and NL PorB induced no significant changes in IL-4 and IL-10 production.

For inflammatory cytokines IL-6 and TNF-α, the cytokine data in FIGS. 10K-O show immunization of mice with PorB/VD2 induced production of IL-6 and TNF-α, For the other constructs, immunization with PorB/VD1, PorB/VD3, PorB/VD4 and NL PorB induced no significant changes in IL-6 and TNF-α production.

These data together indicate that the constructs of compositions herein induce significant amounts of the types of cytokines associated with a robust immune response and do not significantly affect inflammatory cytokines. High amounts of production of IL-12p70 and particularly IFN-γ are known to be important for adequate protection against *Chlamydia*. The results show that immunization of mice with PorB/VD1, PorB/VD2, PorB/VD3, PorB/VD4 and NL PorB induced a robust production of Th1 cytokines IFN-γ and IL-12p70.

Example 11. Antibody Subclass Production in Sera from Immunized Mice

Changes in anti-PorB/VD antibody subclass production were observed in mice immunized subcutaneously with PorB/VD1, PorB/VD2, PorB/VD3, PorB/VD4 and NL PorB. See, FIGS. 11A-E. Mice immunized with each of PorB/VD1, PorB/VD2 and PorB/VD3 showed significant increases in anti-PorB/VD IgG2b antibody levels and smaller increases in IgG1, IgG2c and IgG3 levels compared to pooled pre-immune sera. See, FIGS. 11A-C. Mice immunized with PorB/VD4 showed increased production of anti-PorB/VD4 IgG1, IgG2b antibody subclasses and lower increases of IgG2c and IgG3 levels compared to pooled pre-immune sera data. See, FIG. 11D. Mice immunized with NL PorB showed increases in anti-NL PorB IgG1 and IgG2b antibody levels and little to no increase in IgG2c and IgG3 levels. See, FIG. 11E.

Figure 12B:
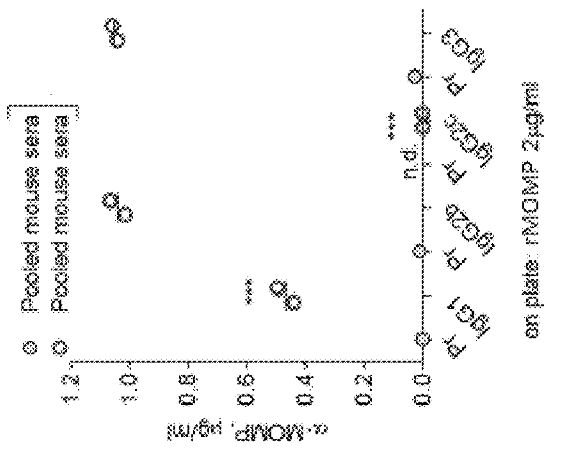

Immunizing mice with MOMP, FIGS. 12A-B, produces anti-MOMP (α-MOMP) which reacts with both nMOMP and rMOMP. ELISA to determine IgG subclasses revealed that more different types of antibody molecules in the polyclonal sera were elicited to antigens present in rMOMP compared to nMOMP. Thus IgG1, IgG2b and IgG3 were observed in the sera to react with rMOMP, and IgG3 reacts with nMOMP.

Example 12. Cross Reactions

ELISA quantification of sera for the activities of anti-PorB/VD1, anti-PorB/VD2, anti-PorB/VD3, anti-PorB/VD4, and anti-NL PorB, each analyzed on plate with 2 μg/ml NL PorB is shown in FIG. 13A. The anti-PorB/VD sera were observed to have cross reacted with antigen NL PorB. NL PorB is the PorB porin from *N. lactamica* (the loop exposed protein used for recombinant display of *Chlamydia* MOMP variable domains herein) expressed recombinantly and purified. These data and those of FIGS. 13B and 13C indicate that an anti-chlamydial immune reaction resulting from immunizations with the vaccine compositions herein includes antibodies against cells of *Neisseria*. These organisms also are pathogens that are sexually transmitted, hence these anti-chlamydial vaccines might have a positive side effect benefit of protecting against multiple diseases.

The results in FIG. 14 on the right show that anti-MOMP sera cross-reacted with PorB/VD1, PorB/VD3, PorB/VD4, PorB/VD1-2-3-4, nMOMP and rMOMP, and did not cross-react with PorB/VD2 nor with NL PorB antibodies as seen by lack of color in dots 8 and 12. These results indicate that antibodies obtained by immunization of mice with MOMP cross-react with the PorB/VD1, PorB/VD3, PorB/VD4, and PorB/VD1-2-3-4 proteins and did not react with either PorB/VD2 or NL PorB. Control spots of nMOMP and rMOMP reacted with anti-MOMP, the reaction with rMOMP giving a stronger signal.

Example 13. Immunization in Animals and Considerations for Humans

PorB/VD hybrid antigens were observed in Examples herein to have induced high levels of specific antibodies that recognize the *Chlamydia* MOMP VDs, and immunization with these antigens in combinations with adjuvants was observed to have favored development of Th1-cell mediated immunity. Immunization with individual and/or combined PorB/VDs and Th1-skewing adjuvants induced production of antigen-specific serum IgG1 and IgG2a, comparable to the effect of native MOMP preparations. Antigen-specific IgG levels were measured, and serum levels of this antibody, which is strongly associated with mucosal immune responses, were observed. Production of Th1-type cytokines in the sera of PorB/VD hybrids-immunized mice, specifically IL-12 and IFN-γ, and of TNF-α, was amplified and sustained through the Th1-skewing effect of the adjuvants used. These cytokines are essential for protection from *Chlamydia* infection (Olsen et al. 2015, Ibid.), while Th2-type cytokines such as IL-10, IL-4 and IL-5 are associated with pathology (Igietseme et al. 2000, Ibid.). See FIGS. 10A-J.

Th2 cytokines were also measured. Low serum levels of IL-10 and IL-4 were observed, due to the effect of CpG DNA and Montanide ISA 720 as adjuvants, and because the immune system of the C57Bl/6 mouse strain is intrinsically biased towards Th1 responses. To elicit reproductive tract mucosal immunity, mucosal delivery of PorB/VD antigens is used with appropriate mucosal adjuvants in mice and production of neutralizing IgG and IgA in sera and in vaginal washes are assessed.

The gut and respiratory tract where the mucosal-associated lymphoid tissue (MALT) is more developed (Gold et al., *J. Infect. Dis.* 1978 February; 137(2):112-21) are likely to yield greater immunization than the genital tract, however mucosal vaccination at these sites are envisioned herein. Combined systemic and mucosal vaccine administration is assessed, for example intranasal and systemic delivery, as vaccination routes for potential human application. Antibodies against the carrier protein, PorB are also measured. *N. lactamica* is a common human nasopharyngeal commensal carried by a large majority of individuals, especially early in life (Gold et al. 1978 Ibid.; Cartwright et al., *Epidemiol. Infect.* 1987 December; 99(3):591-601) and may contribute to natural immunity against *N. meningitidis* (Deasy et al., *Clin. Infect. Dis.* 2015 May 15; 60(10):1512-20). Immunization with *N. lactamica* outer membrane vesicles (OMVs) can elicit meningococcal-neutralizing antibodies (Oliver et al., *Infect. Immun.* 2002 July; 70(7):3621-6; Li et al. *Infect. Immun.* 2006 November; 74(11):6348-55). Immunity to *N. lactamica* may have an impact on commensal carriage and natural immunity, and may affect *N. meningitidis* infections (Troncoso et al. *FEMS Immunol. Med. Microbiol.* 2002 Sep. 6; 34(1):9-15).

In humans, some levels of specific anti-*N. lactamica* PorB antibodies may be naturally present. This antigen fails to induce human polyclonal B cell proliferation and has a scarce cross-reactivity with meningococcal PorB (Vaughan et al., *Ig. J. Immunol.* 2010 Sep. 15; 185(6):3652-60). Thus, a detrimental immune response against *N. lactamica* is unlikely to be observed in human trials following immunization with PorB/VDs. A strategy shown here is to replace the surface-exposed loops of PorB with the MOMP VDs, reducing the PorB antigenicity and increasing that of MOMP. In the event of production of antibodies directed to the β-barrel region of PorB, these would not efficiently recognize PorB when expressed within the bacterial membrane, since this region is normally buried in the bacterial membrane.

The efficacy of the PorB/VD antigens in preventing *Chlamydia* infections is assessed in the mouse model of genital challenge with *C. muridarum*. Then the methods and compositions of recombinant antigens containing combinations of MOMP VDs from the most common human *C. trachomatis* serovars (Wang et al., *J. Infect. Dis.* 1985 October; 152(4):791-800), are applied for a broad protection against this pathogen in humans.

What is claimed is:

1. A composition for vaccinating a subject against an infection with *Chlamydia*, the composition comprising:

a recombinant *Neisseria* porin protein containing at least one antigenic variable domain of a surface protein of the *Chlamydia.*

2. The composition according to claim 1 further comprising at least one selected from the group consisting of: an adjuvant, a pharmaceutically acceptable buffer, a salt, and a carrier.

3. The composition according to claim 1, wherein the antigenic variable domain is at least one portion of a *Chlamydia* major outer membrane protein (MOMP) selected from the group consisting of: SEQ ID NO: 11, SEQ ID NO: 12, SEQ ID NO: 13, and SEQ ID NO: 14.

4. The composition according to claim 3, wherein the antigenic variable domain of the *Chlamydia* MOMP is engineered to be displayed on an exposed surface of the recombinant protein.

5. The composition according to claim 1, wherein the recombinant protein is *Neisseria* PorB porin.

6. The composition according to claim 5, wherein the antigenic variable domain is located on at least one loop of the *Neisseria* recombinant protein.

7. The composition according to claim 1, wherein the recombinant protein has at least one of a secondary, tertiary, and quaternary structure conformation of a native *Neisseria* porin protein.

8. The composition according to either claim 3, wherein the antigenic variable domain of the *Chlamydia* MOMP is a portion of at least one surface-exposed loop.

9. The composition according to claim 6, wherein the loop of the *Neisseria* recombinant protein is at least one selected from the group consisting of loops: 1 (SEQ ID NO: 3), 4 (SEQ ID NO: 6), 5 (SEQ ID NO: 7), 6 (SEQ ID NO: 8), 7 (SEQ ID NO: 9), and 8 (SEQ ID NO: 9).

10. The composition according to claim 1, wherein the *Neisseria* recombinant protein is a porin protein from a species selected from the group consisting of: *Neisseria bacilliformis, N. cinerea, N. elongate, N. flavescens, N. lactamica, N. macacae, N. mucosa, N. polysaccharea, N. sicca, N. subflava, N. flava, N. gonorrhoeae*, and *N. meningitidis.*

11. The composition according to claim 3, wherein the variable domain is selected from at least one *Chlamydia* species selected from the group consisting of: *Chlamydia trachomatis, C. pneumoniae, C. muridarum, C. caviae, C. abortus, C. pecorum, C. psittaci*, and *C. suis.*

12. The composition according to claim 1, wherein the variable domain comprises an amino acid sequence selected from the group consisting of SEQ ID NOs: 11-14.

13. A method of making a vaccine for preventing or treating a subject for infection by a *Chlamydia* pathogen comprising:

engineering a nucleic acid construct encoding a recombinant protein of the vaccine by inserting an amino acid sequence encoding polynucleotide for at least one *Chlamydia* major outer membrane protein (MOMP) variable domain selected from the group consisting of: 1, 2, 3, and 4 (SEQ ID NO: 11-14) into a vector encoding a *Neisseria* recombinant protein, and transforming a cell of a standard protein expression species with the vector encoding the vaccine;

expressing in the cell the vaccine from the vector and isolating the recombinant protein; and, administering the vaccine to the subject thereby preventing or treating the infection.

14. The method according to claim 13, wherein the cell is bacterial, the vector is an *Escherichia coli* plasmid and the cell is *E. coli.*

15. The method according to claim 13, wherein the engineering step further comprises inserting at least one *Chlamydia* MOMP variable domain amino acid sequence into a *Neisseria* PorB porin protein amino acid sequence at a position of the *Neisseria* encoding a surface-exposed loop.

16. The method according to claim 13, wherein the method further comprises, after the expressing step, solubilizing the recombinant protein in detergent to form a solution or a micelle suspension.

17. The method according to claim 13, the method further comprising, after the solubilizing step, removing detergent from the solution.

18. A kit comprising a composition for vaccinating a subject against a *Chlamydia* infection, the composition comprising all or a portion of a recombinant *Neisseria* porin protein containing at least one antigenic variable domain of a surface protein of the pathogen, the composition is in a unit dose and further comprises at least one selected from the group consisting of: an adjuvant, a pharmaceutically acceptable buffer, a salt, and a carrier.

19. The kit according to claim 18 wherein the adjuvant is selected from at least one of the group consisting of: CpG oligonucleotides, CpG oligodeoxynucleotides, a water-in-oil emulsion, a monophosphoryl lipid A (MPLA), a squalene-in-water emulsion, an imidazoquinoline derivative, and a saponin.

20. The kit according to claim 18 wherein the antigenic variable domain is at least one *Chlamydia* major outer membrane protein (MOMP) selected from the group consisting of: SEQ ID NO: 11, SEQ ID NO: 12, SEQ ID NO: 13, and SEQ ID NO: 14.

21. The kit according to claim 18 wherein the recombinant protein is *Neisseria* PorB porin.

* * * * *